US007060689B2

(12) United States Patent
Goins et al.

(10) Patent No.: US 7,060,689 B2
(45) Date of Patent: Jun. 13, 2006

(54) METHODS AND COMPOSITIONS FOR DELIVERY AND RETENTION OF ACTIVE AGENTS TO LYMPH NODES

(75) Inventors: Beth A. Goins, San Antonio, TX (US); William T. Phillips, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 22 days.

(21) Appl. No.: 10/044,650

(22) Filed: Jan. 11, 2002

(65) Prior Publication Data
US 2002/0164648 A1    Nov. 7, 2002

Related U.S. Application Data

(63) Continuation of application No. PCT/US00/18135, filed on Jun. 30, 2000.

(60) Provisional application No. 60/143,742, filed on Jul. 14, 1999.

(51) Int. Cl.
*A01N 43/04*    (2006.01)
*A61K 31/70*    (2006.01)
*A61K 51/00*    (2006.01)
*A61M 36/14*    (2006.01)
*B32B 15/02*    (2006.01)

(52) U.S. Cl. .................. 514/44; 424/121.1; 428/402.2; 440/458

(58) Field of Classification Search ...................... None
See application file for complete search history.

(56) References Cited

U.S. PATENT DOCUMENTS

| | | | |
|---|---|---|---|
| 4,310,505 A | 1/1982 | Baldeschwieler et al. ....... | 424/1 |
| 4,789,736 A | 12/1988 | Canning et al. .............. | 534/14 |
| 4,863,713 A | 9/1989 | Goodwin et al. ............ | 424/1.1 |
| 4,904,479 A | 2/1990 | Illum ........................ | 424/490 |
| 4,948,590 A * | 8/1990 | Hawrot et al. .............. | 424/450 |
| 5,120,526 A | 6/1992 | Fritzberg et al. ............. | 424/1.1 |
| 5,143,713 A * | 9/1992 | Phillips et al. ............. | 424/1.21 |
| 5,420,105 A * | 5/1995 | Gustavson et al. ............ | 514/2 |
| 5,482,698 A * | 1/1996 | Griffiths .................... | 424/1.41 |
| 5,527,528 A * | 6/1996 | Allen et al. ............... | 424/178.1 |
| 5,601,800 A * | 2/1997 | Katti et al. ................. | 424/1.77 |
| 5,690,907 A * | 11/1997 | Lanza et al. ................. | 424/9.5 |
| 5,698,405 A | 12/1997 | Goldenberg ................. | 435/7.5 |
| 5,716,594 A | 2/1998 | Elmaleh et al. ............ | 424/1.41 |
| 5,736,119 A | 4/1998 | Goldenberg et al. ....... | 424/1.53 |
| 5,776,094 A | 7/1998 | Goldenberg ................. | 604/20 |
| 5,792,475 A | 8/1998 | Davis et al. ................ | 424/489 |
| 6,271,209 B1 * | 8/2001 | Smith et al. ................. | 514/44 |
| 6,521,211 B1 * | 2/2003 | Unger et al. ............... | 424/9.52 |
| 2002/0187141 A1 * | 12/2002 | Goldenberg ............. | 424/130.1 |

OTHER PUBLICATIONS

Oussoren et al. Liposomes to target lymphatics by subcutaneous administration. 2001. Advanced Drug Delivery Reviews, 50, pp. 143-156.*
Alving, "Liposomes as carriers of antigens and adjuvants," *J. Immuno Methods*, 140:1-13, 1991.
Barth et al., "Boron neutron capture therapy of cancer," *Cancer Res.*, 50:1061-1070, 1990.
Bayer and Wilchek, "Avidin- and Streptavidin-containing probes," *Methods in Enzymology*, 184:174-187, 1990.
Bookman, "Biologic therapies for gynecologic cancer," *Curr. Opin. Oncol.*, 7(5):478-484, 1995.
Chinol et al., "Biochemical modifications of avidin improve pharmacokinetics and biodistribution, and reduce immunogenicity," *Brit. J. Cancer*, 78(2):189-197, 1998.
Coleman, "Chemical sensitizers and protectors," *Int. J. Radiation Onc. Biol. Phys.*, 42(4):781-783, 1998.
Corely et al., "Binding of biotinated-liposomes to streptavidin is influenced by liposome composition," *Biochim. Biophsy Acta*, 1195:149-156, 1994.
Cox et al., "Guidelines for sentinel node biopsy and lymphatic mapping of patients with breast cancer," *Ann. Surg.*, 227(5):645-653, 1998.
Daemen et al., "Liposomes and virosomes as immunoadjuvant and antigen-carrier systems in vaccine formulations," In: *Medical Applications of Liposomes*, Lasic and Papahadjopoulos (eds), Elsevier Science B.V., 117-143, 1998.
DeCicco et al., "Lymphoscintigarphy and radioguided biopsy of the sentinel axillary node in breast cancer," *J. Nucl. Med.*, 39(12):2080-2084, 1998.
DeFrees et al., "Sialyl Lewis X liposomes as a mulivalent ligand and inhibitor of E-selectin mediated cellular adhesion," *J. Am. Chem. Soc.*, 118:6101-6104, 1996.
DeVita et al., "Principles of cancer management: cancer genetics," In: *Cancer: Principles and Practice of Oncology*, 5th ed., J.B. Lippincott Co., Philadelphia, PA, Chapter 14: 285-293, 1997.
Gabizon et al., "Targeting folate receptor with folate linked to extremities of Poly(ethylene glycol)-grafted liposomes: in vitro studies," *Bioconjugate Chem.*, 10:289-298, 1999.

(Continued)

*Primary Examiner*—Joseph Woitach
*Assistant Examiner*—Robert M. Kelly
(74) *Attorney, Agent, or Firm*—Fulbright & Jaworski L.L.P.

(57) ABSTRACT

The present invention is directed to delivery and retention of active agents to targeted lymph nodes in a mammal using a ligand/anti-ligand pair. More particularly, the invention involves methods, compositions, and kits for delivery and retention of active agents to targeted lymph nodes using compositions comprising a ligand-colloid moiety and compositions comprising an anti-ligand. Active agents may be associated with one or more of the colloid, ligand, or anti-ligand. Conjugation of the ligand and anti-ligand after administration permits retention of aggregated colloid complex in targeted lymph nodes.

21 Claims, No Drawings

OTHER PUBLICATIONS

Goodman et al., *The Pharmacological Basis of Therapeutics*, Gilman et al. (eds), Macmillan Publishing Co., New York, 1985.

Goodwin et al., "Pre-targeted immunoscintigraphy of murine tumors with indium-111-labeled bifunctional haptens," *J. Nucl. Med.*, 29(2):226-234, 1988.

Gregoriadis et al., "DNA vaccination: a role for liposomes," In: *Medical Applications of Liposomes*, Lasic and Papahadjopoulos (eds), Elsevier Science B. V., 61-73, 1998.

Gregoriadis, "Liposomes as immunological adjuvants," *The Theory and Practical Application of Adjuvants*, 7:145-169, 1995.

Griffiths et al., "Direct radiolabeling of monoclonal antibodies with generator-produced Rhenium-188 for radioimmunotherapy: labeling and animal biodistribution studies," *Cancer Res.*, 51(17):4594-4602, 1991.

Hader et al., "Sentinel lymph node biopsy using lymphoscintigraphy," *AORN J.*, 68:572-588, 1998.

Heeremans et al., "Fibrin binding of plasminogen coated liposomes in vitro," *Thromb Haemost.*, 75(1):134-139, 1996.

Hermanson, "Preparation of antibody—liposome conjugates," In: *Bioconjugate Techniques*, Academic Press, San Diego, CA, p. 552-553, 1996.

Hermanson, "Use of glycolipids and lectins to effect specific conjugations," In: *Bioconjugate Techniques*, Academic Press, San Diego, CA, p. 548-549, 1996.

Hirnle, "Liposomes for drug targeting in the lymphatic system," *Hybridoma*, 16(1):127-132, 1997.

Hnatowich et al., "Improved tumor localization with (strept)avidin and labled biotin as a substitute for anitbody," *Nucl. Med. Biol.*, 20:189-195, 1993.

Hnatowich et al., "Investigations of avidin and biotin for imaging applications," *J. Nucl. Med.*, 28(8):1294-1302, 1987.

Hope et al., "Production of large unilamellar vesicles by a rapid extrusion procedures. Characterization of size distribution, trapped volume and ability to maintain a membrane potential," *Biochim. Et Biophys. Acta*, 812:55-65, 1985.

Jeong et al., "Avidin-biotin system for targeting metastases: basic aspects," In: *Handbook of Targeted Delivery of Imaging Agents*, Chapter 18:305-319, CRC Press, 1995.

Johnsson et al., "Optimization of drug loading procedures and characterization of liposomal formulations of two novel agents intended for boron neutron capture therapy (BNCT)," *J. Liposome Res.*, 9(1):53-79, 1999.

Kalofonos et al. "Imaging of tumor in patients with indium-111-labeled biotin and streptavidin-conjugated antibodies: preliminary communication," *J. Nucl. Med.*, 31(11):1791-1796, 1990.

Kang and Pardridge, "Use of neutral avidin improves pharmacokinetics and brain delivery of biotin bound to an avidin-monoclonal antibody conjugate," *J. Pharm. Experimental Therapeutics*, 269:344-350, 1994.

Klibanov et al., "Blood clearance of radiolabled antibody: enhancement by lactosamination and treatment with biotin-avidin or anti-mouse IgG antibodies," *J. Nucl. Med.*, 29(12):1951-1956, 1988.

Klibanov, "Targeted delivery of gas-filled microspheres, contrast agents for ultrasound imaging," *Adv. Drug Delivery Rev.*, 37:139-157, 1999.

Kohno et al., "Drug delivery systems for infection: liposome-incorporating antimicrobial drugs," *J. Infect Chemother.*, 4:159-173, 1998.

Komura et al., "Thermal neutron capture therapy of malignant melanoma using 10B-monoclonal antibodies: in vitro and in vivo analysis," *Melanoma Res.*, 1(5-6):397-403, 1991.

Kotz, "Advancing medical care: the role of nuclear medicine in radioguided surgery," *J. Nucl. Med.*, 39(12):13N-21N, 1998.

Krag et al., "Surgical resection and radiolocalization of the sentinel lymph node in breast cancer using a gamma probe," *Surg. Oncol.*, 2:335-339, 1993.

Krag et al., "The sentinel node in breast cancer—a multicenter validation study," *N. Engl. J. Med.*, 339(14):941-946, 1998.

Krause, "Delivery of diagnostic agents in computed tomography," *Adv. Drug Delivery Rev.*, 37:159-173, 1999.

Kung et al., "Antibody-bering liposomes improve agglutination of latex particles used in clinical diagnostic assays," *Biochim. Biophys. Acta*, 839:105-109, 1985.

Lasic and Pearlman, "Liposomes and lipidic particles in gene therapy," In: *Vesicles*, Marcel Dekker, New York, 477-489, 1996.

Leserman et al., "Ligand targeting of liposomes," In: *Liposomes from Biophysics to Therapeutics*, Ostro (ed), Marcel Dekker, New York, p. 157-194, 1987.

Lindblad, "Aluminium adjuvants," *Theory Prac. Appl. Adjuvants*, 2:21-35, 1995.

Litzinger and Huang, "Amphipathic poly(ethylene glycol) 5000-stabilized dioleoylphosphatidylethanolamine liposomes accumulate in spleen," *Biochim Biophys. Acta*, 1127(3):249-254, 1992.

Magnani et al., "Quantitative comparison of direct antibody labeling and tumor pretargeting in Uveal melanoma," *J. Nucl. Med.*, 37(6):967-971, 1996.

Mayer et al., "Vesicles of variable sizes produced by a rapid extrusion procedure," *Biochim Biophys Acta*, 858:161-168, 1986.

Mayhew et al., "High-pressure continuous-flow system for drug entrapment in liposomes," *Methods Enzym.*, 149:64-77, 1987.

Meares et al., "Macrocyclic chelates of radiometals for diagnosis and therapy," *Br. J. Cancer*, 62 (Suppl 10):21-26, 1990.

Moghimi and Rajabi-Siahboomi, "Advanced colloid-based systems for efficient delivery of drugs and diagnostic agents to the lymphatic tissues," *Prog. Biophys. Molec. Biol.*, 65:221-249, 1996.

Moghimi et al., Surface engineered nanospheres with enhanced drainage into lymphatics and uptake by macrophages of the regional lymph nodes, *FEBS Letters*, 344:25-30, 1994.

Morton et al., "Management of early-stage melanoma by intraoperative lymphatic mapping and selective lymphadenectomy," *Surg. Oncol. Clin. N. Am.*, 1:247-259, 1992.

Morton et al., "Technical details of intraoperative lymphatic mapping for early stage melanoma," *Arch. Surg.*, 127(4):392-399, 1992.

New, "Preparation of liposomes," In: *Liposomes: A Practical Approach*, New (ed), Oxford University Press, NY 33-104, 1990.

Oehr et al., "Streptavidin and biotin as potential tumor imaging agents," *J. Nucl. Med.*, 29:728-729, 1988.

Ogihara-Umeda et al., "Rapid diagnostic imaging of cancer using radiolabeled liposomes," *Cancer Detection and Prevention*, 21(6):490-496, 1997.

Okuhata, "Delivery of diagnostic agents for magnetic resonance imaging," *Advanced Drug Delivery*, 37:121-137, 1999.

Oussoren and Storm, "Lymphatic uptake and biodistribution of liposomes after subutaneous injection: III. Influence of surface modifications with Poly(ethyleneglycol)," *Pharm Res.*, 14(10):1479-1484, 1997.

Oussoren et al., "Lymphatic uptake and biodistribution of liposomes after subcutaneous injection. II. Influence of liposomal size, lipid composition and lipid dose," *Biochim, Biophys. Acta*, 1328:261-272, 1997.

Paganelli et al., "Monoclonal antibody pretargetting techniques for tumour localization: the avidin-biotin system," *Nucl. Med. Commun.*, 12(3):211-234, 1991.

Paganelli et al., "Potential of the avidin-biotin system for diagnostic application," In: *Handbook of Targeted Delivery of Imaging Agents*, Chap. 17, CRC Press, 289-303, 1995.

Paganelli et al., "The three-step pretargeting approach reduces the human anti-mouse antibody response in patients submitted to radioimmunoscintigraphy and radioimmunotherapy," *Eur. J. Nucl. Med.*, 24(3):350-351, 1997.

Paganelli et al., "Three-step monoclonal antibody tumor targeting in carcinoembryonic antigen-positive patients," *Cancer Res.*, 51(21):5960-5966, 1991.

Paganelli et al., "Two-step tumour targetting in ovarian cancer patients using biotinylated monoclonal antibodies and radioactive streptavidin," *Eur. J. Nucl. Med.*, 19(5):322-329, 1992.

Papisov et al., "Drug delivery to lymphatic tissue," *Crit Rev. Ther. Drug Carrier Syst.*, 13(1&2):57-84, 1996.

Phillips and Goins, "Targeted delivery of imaging agents by lipsomes," In: In: *Handbook of Targeted Delivery of Imaging Agents*, Chap. 10, CRC Press, 149-173, 1995.

Phillips et al., "Novel method of greatly enhanced delivery of anti-cancer agents to lymph nodes," 9th *Annual Symposium on Cancer Research in San Antonio*, Abstract #, Jul. 16, 1999.

Pykett, "NMR imaging in medicine," *Sci Am.*, 246(5):78-88, 1982.

Rao et al., "A trivalent system from vancomycin-$_D$-Ala-$_D$-Ala with higher affinity than avidin-biotin," *Science*, 280(5364):708-711, 1999.

Rawls, "Bringing Boron to bear on cancer. Chemists near goal of delivering a billion $^{10}$B atoms selectively to cells to target them for destruction via neutron capture therapy," *C&EN*, 26-29, Mar. 22, 1999.

Reintgen, "The role of lymphoscintigraphy in lymphatic mapping for melanoma and breast cancer," *J. Nucl. Med.*, 39(12):22N-36N, 1998.

Runge et al., "Paramagnetic agents for contrast-enhanced NMR imaging: a review," *Am. J. Roentgeno*, 141(6):1209-1215, 1983.

Schechter et al., "Indirect immunotargeting of CIS-PT to human epidermoid carcinoma KB using the avidin-biotin system," *Int. J. Cancer*, 48:167-172, 1991.

Schuber, "Chemistry of ligand-coupling to liposomes," In: *Liposomes as Tools in Basic Research and Industry*, Philippot and Schuber (eds.), CRC Press, Boca Raton, 21-39, 1995.

Sigma Catgalog, Alphabetical list of compounds, 149-150, 1999.

Sinitsyn et al., "Rapid blood clearance of biotinylatd IgG after infusion of avidin," *J. Nucl. Med.*, 30(1):66-69, 1989.

Sinkula and Yalkowsky, "Rationale for design of biologically reversible drug derivatives: prodtugs," *J. Pharm. Sci.*, 64:181-210, 1975.

Stickney et al., "Bifunctional antibody: a binary radiopharmaceutical delivery system for imaging colorectal carcinoma," *Cancer Res.*, 51(24):6650-6655, 1991.

Strand and Bergqvist, "Radiolabeled colloids and macromolecules in the lymphatic system," *Crit. Rev. Ther. Drug Carrier Syst.*, 6(3):211-237, 1989.

Swinyard, "Analgesics and antipyretics," *Remington's Pharmaceutical Sciences, 15th ed.*, pp. 1035-1038 and 1570-1580.

Tanabe and Reintgen, "The role of sentinel lymph node mapping for melanoma," *Adv. Surg.*, 31:79-103, 1998.

Terskikh et al., "Peptabody: a new type of high avidity binding protein," *Proc. Natl. Acad. Sci. USA*, 94:1663-1668, 1997.

Tiong et al., "Comparison of conventional adjuvants and "adjuvant-free" monoclonal antibody targeting for stimulating antibody responses against a conjugate of luteinizing hormone releasing hormone and avidin," *Vaccine*, 11(4):425-430, 1993.

Tiourina et al., "Evaluation of surgical gamma probes for radioguided sentinel node localisation," *Eur. J. Nucl. Med.*, 25(9):1224-1231, 1998.

Van der Veen et al., "Gamma probe-guided sentinel node biopsy to select patients with melanoma for lymphadenectomy," *Br. J. Surg.*, 81(12):1769-1770, 1994.

Veronesi et al., "Sentinel-noed biopsy to avoid axillary dissection in breast cancer with clinically negative lymphnodes," *Lancet*, 349(9069):1864-1867, 1997.

Weiss et al., *Lymphatic System Metastasis*, Hall, Boston, 1980.

Wilbur et al., "Biotin reagents for anitbody pretargeting. 3. Synthesis, radioiodination, and evaluation of biotinylated starburst dendrimers," *Bioconjugate Chem.*, 9:813-825, 1998.

Wolf, "Specific imaging agents for lymph nodes," In: *Handbook of Targeted Delivery of Imaging Agents, Chap. 21*, 365-384, CRC Press, 1995.

Woodle and Leserman, "Liposomal antisense oligonucleotide therapeutics," *Lasic and Papahadjopoulos (eds.) Medical Applications of Liposomes*, Elsevier Science B. V., 429-449, 1998.

Yoffrey and Courtice, *Lymphatics, lymph and the lymphomyeloid complex*, Academic Press, London, 1970.

Yuan et al., "Pharmacokinetic analysis of two-step approaches using bifunctional and enzyme-conjugated anitbodies," *Cancer Res.*, 51(12):3119-3130, 1991.

* cited by examiner

METHODS AND COMPOSITIONS FOR DELIVERY AND RETENTION OF ACTIVE AGENTS TO LYMPH NODES

This is a continuation of co-pending international application PCT/US00/18135 filed Jun. 30, 2000, which claims priority of then co-pending U.S. Provisional Application No. 60/143,742, filed Jul. 14, 1999.

The government owns rights in the present invention pursuant to grant number R01-HL53052 from the National Institutes of Health.

BACKGROUND OF THE INVENTION

1. Field of the Invention

The present invention relates generally to delivery and retention of active agents at a targeted site using compositions comprising ligand and anti-ligand conjugates. More particularly, certain embodiments concern methods, compounds, compositions and kits useful for targeted delivery and retention of agents at specific lymph nodes by administration of a composition comprising a ligand-colloid moiety and a composition comprising an anti-ligand. In certain embodiments the ligand is one member of the biotin/avidin pair and the anti-ligand is the other member of the biotin/avidin pair.

2. Description of Related Art

Avidins are a family of proteins functionally defined by their high affinity for binding biotin. Avidins are small oligomeric proteins made up of four identical subunits, each with a single binding site for biotin. Avidins include proteins (1) present in the eggs of amphibians, reptiles, and birds, and known as avidin, and (2) produced by *Streptomyces avidinii* and known as streptavidin. Streptavidin is similar to avidin in its binding properties, but has lower non-specific tissue binding, and therefore often is used in place of avidin. However, the immunogenicity of streptavidin is a major drawback to its use. Paganelli et al., *Eur J Nucl Med* 24(3):350–351, 1997. Consequently, modified avidins with lower immunogenicity than that of streptavidin have been developed. Chinol et al., *Brit J Cancer* 78(2): 189–197, 1998; Goldenberg, U.S. Pat. No. 5,698,405, incorporated herein in their entirety by reference. Chinol et al. found that conjugating avidin to monomethoxypolyethyleneglycol 5000 (mPEG), in particular an average of 7 mPEG chains per avidin molecule, produced a compound with substantially reduced immunogenicity and low cross-reactivity with native avidin. Goldenberg reduced the immunogenicity of avidin by coupling it with a carbohydrate polymer or polyol groups. As used hereafter, "avidin" includes all of the above proteins.

Biotin is a natural water-soluble vitamin found in every living cell. Several derivatives of biotin are commercially available. Due to the extremely high affinity of avidins for biotin, the biotin/avidin system has been used for targeting, detecting, and treating tumors. The tetravalency of avidin for biotin permits amplification when avidin binds to biotin.

The biotin/avidin system has been used primarily in conjunction with antibodies targeting specific tissues or lesions, as described, for example, in Hnatowich et al., *Nucl Med Biol* 20:189–195, 1993; Ogihara-Umeda et al., *Cancer Detection and Prevention* 21(6):490–496, 1997; Lanza, U.S. Pat. No. 5,690,907; Goldenberg, U.S. Pat. Nos. 5,736,119 and 5,776,094; and Griffiths, U.S. Pat. No. 5,482,698, incorporated herein in their entirety by reference. Antibodies directed against different determinants associated with pathologic or normal cell type or pathogenic organisms, wherein avidin or biotin is conjugated to the targeting antibody, have been used to target tissues and lesions, as described in, for example, Griffiths, U.S. Pat. No. 5,482,698 and Goldenberg, U.S. Pat. No. 5,776,094. In such applications, the biotin/avidin system has been used as a means for delivering a detection agent to a site previously targeted by antibody and for clearing excess targeting antibody from the circulation in order to increase the target:background ratio.

Two basic approaches for targeting specific sites in a subject with biotin/avidin systems have been used in mammalian subjects. In a 2-step procedure, a targeting antibody is conjugated with either avidin or biotin and then is injected into a subject, thus localizing the avidin or biotin at a site of interest. Thereafter, either biotin or avidin (depending on which was coupled to the targeting antibody) bearing an active agent is injected and is localized at the site of the primary antibody by binding to avidin or biotin respectively. Timing of the second injection after the first one is very critical. Injecting the active agent-avidin (or biotin) too early will increase the avidin/biotin conjugates in the bloodstream and nontargeted tissues, while injecting too late may decrease the amount targeted to the desired site because of reduced retention of the primary antibody at the tumor.

Incomplete clearance of unbound antibody from the blood circulation can obscure detection of the target site. In the second method for targeting specific sites with the biotin/avidin system, blood background is reduced by injecting biotinylated antibodies followed three days later by cold (unlabeled) avidin. The resultant circulating biotinylated antibody-avidin complexes are sequestered from the blood by the liver. Radioactive biotin is then injected and binds to the antibody-biotin-avidin complexes already localized at the targeted site.

A drawback of both of the above approaches for targeting tumors is that they require that a subject be available to undergo multiple procedures over a prolonged time, generally a few days.

Essential to known uses of the biotin/avidin system for detection and therapy of specific sites in the body, such as tumors, is the element of "pretargeting," as described, for example, in Hnatowich et al, *J Nucl Med* 28(8):1294–1302, 1987; Paganelli et al., *Nucl Med Commun* 12(3):211–234, 1991; Paganelli et al., *Eur J Nucl Med* 19(5):322–329, 1992; Griffiths, U.S. Pat. No. 5,482,698, Goodwin et al., U.S. Pat. No. 4,863,713; Goodwin et al., *J Nucl Med* 29(2):226–234, 1988; Oehr et al., *J Nucl Med* 29:728, 1988; Klibanov et al., *J Nucl Med* 29(12):1951–1956, 1988; Sinitsyn et al., *J Nucl Med* 30(1):66–69, 1989; Kalofonos et al., *J Nucl Med* 31(11):1791–1796, 1990; Schechter et al., *Int J Cancer* 48(2):167–172, 1991; Paganelli et al., *Cancer Res* 51(21): 5960–5966, 1991; Stickney et al., *Cancer Res* 51(24):6650–6655, 1991; and Yuan et al., *Cancer Res* 51(12):3119–3130, 1991; all incorporated herein in their entirety by reference. Pretargeting makes use of the biotin/avidin system to eliminate detection and therapeutic agents from sites other than the targeted sites. Pretargeting does not make use of the biotin/avidin system to directly target sites, as occurs with the present invention.

In pretargeting, a targeting compound comprising a targeting moiety such as antibody conjugated to one member of the biotin/avidin pair is administered to a subject. A portion of the targeting compound distributes to the targeted site and is bound there. The significant portion of the targeting compound may be retained in the blood pool. After a predetermined time period, typically a few hours to two to three days, a compound comprising the member of the biotin/avidin system that is not conjugated to a targeting moiety is administered and binds with the biotin or avidin of the circulating targeting compound. A detection or therapeutic agent is incorporated with either the targeting compound, or the subsequently injected avidin or biotin compound, or both, prior to administration. When bound, the newly formed compound comprising targeting moiety-biotin-avidin-detection/therapeutic agent is removed from circulation by the reticuloendothelial system, thus clearing the compound from those portions of the body that are not targeted and lowering the background level of the compound. This increases the target-to-background ratio and increases the ability to detect the targeted site High background levels of a detection agent have long been recognized as a major impediment to achieving the high target: background ratios desirable for detection of lesions. Furthermore, high background levels of therapeutic agents can lead to toxicity and restrict the therapeutic agents and dosages that can be safely used for therapy.

Liposomes have been described as potential agents for targeted delivery of diagnostic or therapeutic agents to a wide range of organ systems and diseases. Such targeting is due primarily to a physical feature of the liposome, such as size, charge, and lipid compound, and is not due to specific site-directed targeting. Phillips et al., *Handbook of Targeted Delivery of Imaging Agents*, CRC Press, 149–173, 1995, incorporated herein in its entirety by reference. Coupling macrophage-specific ligands to the surface of liposomes increases liposome drainage from an interstitial injection site and enhances their localization in regional lymph nodes. Moghimi et al., *Prog Biophys Molec Biol* 65:221–249, 1996, incorporated herein in its entirety by reference.

High background levels of radiolabeled liposomes following intravenous injection can impede the high target: background ratios needed for detection of a lesion. Ogihara-Umeda et al., *Cancer Detection and Prevention* 21(6): 490–496, 1997, demonstrated that radiolabeled liposomes coated with biotin accumulated in a tumor, but that target: background ratios were improved following an intravenous injection of avidin. The avidin was used to remove the remaining radiolabeled biotin-liposomes in the blood circulation by binding together to form crosslinked complexes which were cleared by the liver.

The lymphatic system plays important roles in transporting body fluids and particulate materials from the body's periphery to the thoracic duct, returning large proteins and lymphocytes to the blood circulation from the tissue fluid, and transporting the products of fat digestion in the gastrointestinal tract (chylomicrons) into the blood circulation. The properties of the lymphatic system have been reviewed in detail by Yoffrey et al., *Lymphatics, lymph and the lymphomyeloid complex,* Academic Press, London, 1970, incorporated herein in its entirety by reference. The lymphatic system also plays an important role in the spread of a variety of disease processes, as described, for example, by Papisov et al., *Crit Rev Ther Drug Carrier Syst* 13(1&2): 57–84, 1996, incorporated herein in its entirety by reference. Lymphatic dissemination of disease processes allows the spread of disease to regional lymph nodes, and even further. For example, malignant cells can enter the lymphatic system and become captured by lymph nodes; the lymph nodes consequently serve as foci of residual metastatic cancer, with potential tumor recurrence even after treatment of the primary tumor. Weiss et al., *Lymphatic System Metastases*, Hall, Boston, 1988. The lymph can also be involved in the spread of tumors to other organs. Consequently, there is considerable need for a method of determining and examining lymph nodes involved in the dissemination of disease processes and in delivering therapeutic agents to lymph nodes. This subject has been reviewed extensively by Hader et al;, *AORN J* 68:572–588, 1998, and Tanabe et al., *Advances in Surgery* 31:79–103, 1998, incorporated herein in their entirety by reference.

Any material which transits from the interstitial space to the intralymphatic space will move to a series of lymph nodes, the regional lymph nodes, that drain the lymph toward the thoracic duct. The first such lymph node encountered is the primary lymph node. Lymph from the primary lymph node will pass to subsequent lymph nodes, called secondary lymph nodes.

The sentinel lymph node is the first lymph node encountered by a metastasizing tumor cell after it has entered the lymphatic system. The importance of the sentinel lymph node lies in the fact that metastasizing tumor cells are recognized by the immune system and stopped there. Many times, these tumor cells are destroyed by the immune cells located in the sentinel lymph node. However, tumor cells can survive, creating a foci of metastatic disease in the sentinel lymph node.

If tumor cells have metastasized to other locations in the body, malignant tumor cells will be found in the sentinel lymph node 99% of the time. On the other hand, if no tumor cells are found in the sentinel lymph node after close pathological examination, it is very unlikely that the cancer will reoccur after the primary tumor has been removed For these reasons, it is very important to locate the sentinel lymph node and, if necessary, target treatment specifically to it.

Locating the sentinel lymph node in a mammalian subject is not always easily accomplished. Lymph nodes tend to blend in with the rest of the body tissue. In addition, it is not readily apparent which of numerous lymph nodes identified drains a disease locus, such as a tumor bed. Furthermore, occasionally a disease locus can drain to more than one area, thus there can be multiple sentinel lymph nodes. The present invention addresses the need to identify sentinel lymph nodes.

Previous methods for directing detection or therapeutic agents to lymph nodes have employed colloids, especially liposomes, to passively target lymphatic tissue, as described, for example, in Moghimi et al., *Prog Biophys Molec Biol* 65:221–249, 1996, Davis, U.S. Pat. No 5,792,475; Wolf, in *Handbook of Targeted Delivery of Imaging Agents, Chap.* 21, 366–384, CRC Press, 1995; Papisov et al., *Crit Rev Ther Drug Carrier Syst* 13(1&2):57–84, 1996, all of which are incorporated herein in their entirety by reference. Interstitial administration of colloids such as liposomes results in accumulation of such colloids in lymphatic tissue, and is described, for example, in Oussoren et al., *Biochim Biophys Acta* 1328:261–272, 1997, incorporated herein in its entirety by reference. Efficient accumulation of macromolecular carriers in lymph nodes after intralymphatic injection of macromolecules has also been described. See, for example, Papisov, *Crit Rev Ther Drug Carrier Syst* 13(1&2):57–84, 1996.

Methods for detecting sentinel lymph nodes have been described. In one method microcolloidal particles labeled with a radioisotope are administered interstitially proximal to the tumor site and scintigraphic scans or radio-guided probes are used to locate the site(s) of maximum radioactivity. This method is described, for example, in Van der Veen et al., *Br J Surg* 81(12):1769–1770, 1994; Krag et al., *Surg Oncol* 2:335–339, 1993; Veronesi et al., *Lancet* 349 (9069):1864–1867, 1997, all of which are incorporated herein in their entirety by reference. In another method, vital blue dye is injected peri-tumor, as described, for example, in Morton et al., *Surg Oncol Clin N Am* 1:247–59, 1992 and *Arch Surg* 127(4):392–399, 1992, incorporated herein in their entirety by reference. An intraoperative method for detecting sentinel lymph nodes using both radiolabeled colloid and vital blue dye has also been described, for example, in Cox et al., *Ann Surg* 227(5):645–653, 1998, incorporated herein in its entirety by reference. In this method radiolabeled colloid is injected around the periphery of a tumor site one to six hours prior to an operative procedure. Immediately before the operative procedure, vital blue dye is injected peri-tumor. The vital blue dye stains afferent lymphatic channels to aid in visual localization of the sentinel lymph node. Prior to skin incision, a hand-held gamma-detection probe is used to localize the sentinel lymph node. After incision, the gamma probe is used to guide localization of the sentinel lymph node. See, for example, Kotz, *J Nucl Med* 39(12):13N–21N, 1998; Krag et al., *N Engl J Med* 339(14):941–946, 1998; Reintgen, *J Nucl Med* 39(12):22N–36N, 1998, all of which are incorporated herein in their entirety by reference.

Injection of a radiolabeled colloid to detect the sentinel lymph node by a radioactive probe has been used in conjunction with injection of blue dye to visualize the sentinel lymph nodes. A problem with this approach is that the radiolabeled colloid and the blue dye do not move through the lymphatic system at the same rate. The blue dye is absorbed rapidly from its site of injection and readily passes through lymph nodes. In contrast, the radiolabeled colloid is absorbed more slowly, takes time to accumulate in the lymph node, and does not significantly pass through the first lymph node encountered to other lymph nodes. Consequently, the timing of the localizing surgical procedure is difficult because simultaneous accumulation of blue dye and radiolabeled colloid at the sentinel node requires very different injection times for the blue dye and radiolabeled colloid.

A targeting system for the delivery of diagnostic and therapeutic agents to the lymphatic system should have the following characteristics: (i) spread well from the injection site, (ii) provide good uptake in primary lymph node(s) if sentinel lymph node is desired, and (iii) provide good uptake in secondary regional lymph nodes if desired. Various attempts have been made to increase lymphatic uptake by changes in particle size and particle number and particle nature and these have been reviewed by Moghimi and Rajabi-Siahboomi, *Prog Biophys Molec Biol* 65:221–249, 1996 and Strand, *Crit Rev Ther Drug Carrier Syst* 6(3): 211–238, 1989, incorporated herein in their entirety by reference.

While some methods have been developed for targeting and detecting specific sites in the body of a mammal, what is lacking in the prior art are effective methodologies for targeting specific lymph nodes and retaining active agents, including detection and therapeutic agents, in the targeted lymph nodes

SUMMARY OF THE INVENTION

The present invention relates generally to delivering and retaining a desired agent at a targeted site using a ligand/anti-ligand pair. More particularly, the invention relates to delivering and retaining an active agent at lymph nodes using a ligand/anti-ligand pair. Further, the invention concerns methods, compounds, compositions and kits useful for delivering and retaining an active agent at specific lymph node(s) in a mammal by administration of compositions comprising a detection or therapeutic agent and a ligand/anti-ligand pair. In a preferred embodiment, the ligand/anti-ligand pair is avidin/biotin.

In one embodiment, the present invention features a ligand/anti-ligand system and colloids that are captured by draining lymph nodes when administered to a subject in vivo. Ligand or anti-ligand may be conjugated to the colloid. The ligand may be, for example, biotin The anti-ligand may be, for example, avidin.

In another embodiment, the invention features methods of delivering and retaining an active agent at targeted lymph nodes in a mammal. The methods comprise the steps of (a) administering to a mammal a first composition comprising ligand conjugated to a colloid, and (b) administering to a mammal a second composition comprising anti-ligand in which the anti-ligand binds to the ligand. The anti-ligand may be administered proximal to the site of the colloid-ligand conjugate administration. After the anti-ligand binds the ligand of the colloid-ligand conjugate, the aggregated colloid complex may be retained at the lymph node(s) draining the areas of interest.

In a further embodiment, the colloid comprises a liposome. In some particular the liposome comprises one or more phospholipids. In another embodiment, the liposome comprises DSPC and/or DPPC.

In still another embodiment, the colloid of the invention is associated with, typically by encapsulation or binding, one or more active agents. The active agents may be detection or therapeutic agents. The detection or therapeutic agents are employed to detect or treat the lymph node(s) draining the area of interest.

In yet another embodiment the invention provides a method and composition for delivering and retaining an active agent at the sentinel lymph node(s) comprising the steps of (a) administering to a mammal a first composition comprising ligand conjugated to a colloid, and (b) administering to a mammal a second composition comprising anti-ligand in which the anti-ligand binds to the ligand. The colloid may comprise an active agent, in particular, a blue dye as a detection means. Anti-ligand, with or without an active agent, that binds to the ligand of the ligand-colloid-blue dye composition, may be administered simultaneously or shortly after the ligand-colloid-blue dye composition is administered to a mammal. The preferred administration method is by subcutaneous injection.

In an embodiment of the detection or therapeutic method of the present invention, the ligand-colloid-active agent can be injected subcutaneously or intracavitary. The preferred dose depends on the species and whether a therapeutic or diagnostic agent is administered. This can be administered as a single injection or in divided doses. Simultaneous with the ligand-colloid composition or after 30 minutes, more preferably at less than 15 minutes and even at less than 10 minutes, a dose of anti-ligand, with or without an active agent, may be administered subcutaneously or intracavitary. The anti-ligand can be given as a single injection or in divided doses, administering the anti-ligand in two doses is preferred in certain circumstances. Within one hour of the last injection, detection of lymph nodes containing the aggregated colloid complex is accomplished using, for example, planar and single-photon emission computed tomography scans made with a gamma camera equipped with the appropriate collimator and selecting the appropriate energy windows for the detection isotope being used, such as 140 keV for Technetium-99m. An important point is that the ligand-colloid continues to accumulate in the lymph node and the colloid is retained in the node for a prolonged time (>20 hours).

The invention may be useful in delivering and retaining one or more therapeutic agents at targeted lymph nodes. The invention may also be useful in delivering and retaining one or more diagnostic agents, such as dyes or radioisotopes, at targeted lymph nodes.

In a preferred embodiment, the colloid comprises liposome, the ligand comprises biotin, and the anti-ligand comprises avidin.

Additional features and advantages of the invention will become more apparent from the following detailed description and claims.

DETAILED DESCRIPTION OF ILLUSTRATIVE EMBODIMENTS

Prior to setting forth the invention in detail, it may be helpful to set forth definitions of certain terms to be used within the disclosure.

Targeting Moiety
  A molecule that binds to a defined population of cells or localizes to a specific body tissue.

Ligand/Anti-Ligand System or Pair
  A complementary/anti-complementary set of molecules that demonstrate specific binding, generally of relatively high affinity. A ligand/anti-ligand system or pair useful in the present invention is biotin/avidin.

Ligand
  As defined herein, a "ligand" is a molecule conjugated to the colloid with high affinity for the anti-ligand. Biotin is an example of a ligand useful in the present invention.

Anti-Ligand
  As defined herein, an "anti-ligand" demonstrates high affinity, and preferably, multivalent binding of the complementary ligand. Avidin is an example of an anti-ligand useful in the present invention.

Avidin
  As defined herein, "avidin" includes avidin, streptavidin and derivatives and analogs thereof that are capable of high affinity, multivalent or univalent binding of biotin. Avidins are fairly small oligomeric proteins, made up of four identical subunits, each bearing a single binding site for biotin. Avidins can therefore bind up to four moles of biotin per mole of avidin. Avidins in the present invention include avidins modified to have lower immunogenicity relative to that of natural streptavidin.

Biotin
  As defined herein, "biotin" includes the natural water-soluble vitamin found in every living cell, and the derivatives and analogs capable of being bound by avidin.

Active Agent
  A pharmaceutically or therapeutically active agent or diagnostic agent ("the payload"), including radionuclides, drugs, anti-tumor agents, toxins, dyes, contrast media, and the like. The active agent may be associated with the colloid particles by any well-known technique, but should be in such a way that the active agent remains associated with the colloid particle until at least the point of uptake of the particle by the lymph node.

Conjugate
  A conjugate encompasses chemical conjugates (covalently or non-covalently bound) and the like.

Detection/Therapeutic Agent
  Any agent, compound, or composition that, when administered, can be used for detection or therapy of specific sites within the mammalian body.

Aggregated Colloid Complex
  A composition comprising anti-ligand, which may or may not be conjugated to an active agent, bound to ligand conjugated or bound to a colloid, which may or may not be complexed with an active agent.

Colloid-Ligand-Anti-Ligand Composition
  A composition comprising anti-ligand bound to ligand, which is conjugated or bound to colloid.

Glutathione
  A natural tri-peptide anti-oxidant found in every living cell. Glutathione is used in the present invention as a component of the radiolabeling of liposomes with Technetium-99m using HMPAO.

HMPAO
  Hexamethylpropyleneamine oxime (HMPAO) is a novel lipophilic chelator useful in a novel technique to label liposomes with Technetium-99m. See U.S. Pat. Nos. 4,789,736, 5,143,713, and 5,158,760.

The methods, compounds, compositions, and kits of the present invention are advantageous for selective detection and therapy of lymph nodes because of the significant increase in the amount of the detection and/or therapeutic agent which is available at the targeted lymph node due to the increase in retention of the detection and/or therapeutic agent at the targeted lymph node. These methods, compounds, compositions, and kits are an improvement, in terms of absolute amount of detection and/or therapeutic agent retained at the lymph node, as compared to the prior art procedures which do not contemplate the use of ligand/anti-ligand systems to retain colloids in lymph nodes, thereby amplifying the amount of detection and/or therapeutic agents available at the targeted lymph node. The methods of the present invention can be used to detect (either by internal procedures or by external imaging) and/or treat lymph nodes which drain specific body sites. The delivery and retention of therapeutic and/or detection agents at lymph nodes using colloids such as microspheres, microcapsules, emulsions, and liposomes is contemplated.

The present invention greatly increases the uptake and retention of colloids in regional lymph nodes by use of a ligand/anti-ligand system, for example, the biotin/avidin system, to form complexes which are directed to and retained in the lymphatic system. Methods for coupling ligands to colloids, such as liposomes, are known to those of skill in the art. See, for example, Schuber, in *Liposomes as Tools in Basic Research and Industry*, Philippot and Schuber (eds), CRC Press, Boca Raton, 21–39, 1995, incorporated herein in its entirety by reference. Initial injection of colloid-ligand followed by subsequent injection of anti-ligand causes binding of ligand and anti-ligand, with cross-linking and consequent aggregation of colloid-ligand that is in the process of migrating through lymphatic vessels. The complex of colloid-ligand-anti-ligand-active agent(s) moves from the site of binding of the ligand and anti-ligand to the lymph and onward to the primary lymph node.

The first lymph node encountered, or the chain of draining lymph nodes, can be targeted by the methods disclosed herein. Formation of the aggregated colloid complex prior to reaching the lymph node is important in localizing the active agent at the lymph node. When the aggregated colloid complex reaches the next encountered lymph node, it becomes retained for a prolonged time in this node.

The colloidal particles of the present invention are preferably in the size range 1 to 5,000 nm, more preferably 5–500 nm, and most preferably 50 to 300 nm. Such systems are well transported from the site of injection and are well retained in the lymph nodes (primary and secondary). If the colloid-ligand composition is too large, it is retained at the site of injection. If the colloid-ligand composition is too small, it is transported from the site of injection into the circulation and is not retained in the lymph node(s).

In an embodiment of the method of the present invention, the ligand-colloid-active agent can be administered as a single injection or in divided doses. For example, simultaneous with the ligand-colloid composition or after 2 hours, more preferably at less than 30 minutes and even at less than 10 minutes, a dose of anti-ligand, with or without an active agent, is administered. The anti-ligand composition can be given as a single injection or in divided doses; administering the anti-ligand in two doses is preferred in certain circumstances. The ligand-colloid and anti-ligand compositions are administered by subcutaneous, subdermal, submucosal, intraperitoneal, or intrapleural injection. Within one hour of the last injection, detection of lymph nodes containing the aggregated colloid complex is accomplished. If a radiolabeled detection agent is encapsulated in or attached to the colloid or attached to anti-ligand, detection of the lymph nodes is accomplished using for example, planar and single-photon emission computed tomography scans made with a gamma camera equipped with the appropriate collimator and selecting the appropriate energy windows for the detection isotope being used, such as 140 keV for Technetium-99m. If blue dye is encapsulated in the colloid, the lymph nodes can be visually detected.

In another embodiment, the instant invention features ligand and anti-ligand compositions further comprising an imaging agent and uses for the compositions in detecting and/or monitoring tumors or sites of metastasis in a subject. In one embodiment, the ligand- or anti-ligand-imaging agent-composition is administered in vivo and monitored using a means appropriate for the label. Preferred methods for detecting and/or monitoring a-ligand- or anti-ligand-imaging agent composition in vivo include Gamma Scintigraphy, Positron Emission Tomography (PET), Single Photon Emission Computer Tomography (SPECT), Magnetic Resonance Imaging (MRI), X-ray, Computer Assisted X-ray Tomography (CT), Near Infrared Spectroscopy, and Ultrasound. These techniques provide information regarding detection of neoplastic involvement, particularly of inaccessible nodes in patients with malignant diseases. Knowledge on the size of the node and the filling of nodes can also be instructive.

The particles so directed to the lymph nodes in detection applications will contain suitable contrast or imaging agents such as ferromagnetic materials such as iron oxide, perfluorochemicals such as perfluorooctylbromide, or gamma emitting radiolabels such as Technetium-99m, Indium-111, Gallium-67, Thallium-201, Iodine-131, 125, or 123, positron emitting radiolabels such as Fluorine-18, or those produced by neutron activation such as Samarium-153.

The compositions of the present invention may be administered by standard methods, including intrapleural, intraperitoneal, subcutaneous, intraarticular, intramucosal, intramuscular, intradermal, intratumoral, interstitial, intraorgan, intracavitary, intralymphatic, intralesion, and intraosseal injection. The compositions should satisfy the usual requirements for injection and are therefore administered in sterile, non-pyrogenic and preferably non-inflammatory solutions such as saline. Single or multiple injections can be used for administration of the compositions. The dose administered and volume of solution injected depends on the anatomical area to be treated or investigated and will be readily determined by those of skill in the art.

The time required for initial localization of the colloid-ligand-anti-ligand composition in the lymph node is generally under 1 hour; however, the colloid-ligand-anti-ligand composition continues to accumulate in lymph node for 24 hours or more. Therefore, therapy or imaging can be accomplished in one short procedure. In addition, localization and retention of the colloid-ligand-anti-ligand composition at specific lymph nodes limits the distribution of the colloid-ligand-anti-ligand composition in the circulation, thus the active agents of the colloid-ligand-anti-ligand composition are unlikely to produce toxic side effects at the levels required for therapy or imaging.

An advantage of the present invention is the flexibility of the system. For example, when a biotin-liposome-avidin complex is utilized, the complex is strongly retained in the targeted lymph node for a prolonged period, at least several days, until it is metabolized. If Technetium-99m, whose half-life is 6 hours, is employed as an active agent, it can still be imaged at least 20 hours after administration. If blue dye is employed as an active agent, lymph nodes may be visually detected at least two weeks after administration. X-ray and computerized axial tomography contrast agents may be detected for a prolonged time period, similar to that for detection of blue dye.

An embodiment of the present invention provides methods of increasing active agent localization and retention at a targeted lymph node of a mammalian recipient, which methods comprise:

(1) administering to a mammal a first composition comprising ligand conjugated to a colloid; and, which may contain an active agent, and ligand, for example, biotin;

(2) administering to a mammal anti-ligand which binds the ligand of the first composition.

The colloid may be associated with an active agent, such as a detection or therapeutic agent. The ligand may be, for example, biotin. The anti-ligand, which may or may not be associated with an active agent, may be, for example, avidin. The anti-ligand may be administered simultaneously or immediately after administration of the colloid-ligand composition. The anti-ligand may be administered in the same location as the colloid-ligand or it may be administered at another site so that it encounters the colloid-ligand at, or just prior to reaching, the targeted lymph node.

Another embodiment of the present invention provides methods for detecting a sentinel lymph node of a mammal, which methods comprise:

(1) administering to a mammal a first conjugate comprising ligand conjugated to a colloid; and associated with vital blue dye and which may further contain another active agent, and ligand, for example, biotin;

(2) administering to a mammal anti-ligand, which binds to the ligand of the first composition.

The colloid may be associated with a detection agent, such as a radioisotope or dye. The ligand may be, for example, biotin. The anti-ligand, which may or may not be associated with an active agent, may be, for example, avidin. The anti-ligand may be administered simultaneously or immediately after administration of the colloid-ligand composition.

Yet another embodiment of the invention provides a composition comprising ligand conjugated to a colloid containing a radioactive label and a readily-visualized dye.

The active agent may be associated with the colloid or anti-ligand by any well known technique, but should be in such a way that the active agent remains associated with the colloid or anti-ligand until the point of uptake of the colloid-ligand-anti-ligand complex by the lymph nodes. The association of the active agent with the colloid includes any method of incorporating the active agent into or grafting the active agent onto the colloid.

The lymph node delivery and retention methods and compositions of the present invention will be advantageous for many applications to include:

(1) Imaging and Visualization Modalities of the Lymphatic System such as Gamma Scintigraphy, Positron Emission Tomography (PET), Single Photon Emission Computer Tomography (SPECT), Magnetic Resonance Imaging (MRI), X-ray, Computer Assisted X-ray Tomography (CT), Near Infrared Spectroscopy, and Ultrasound. These techniques provide information regarding detection of neoplastic involvement, particularly of inaccessible nodes in subjects with malignant diseases and can also be applied in other infectious and inflammatory conditions. Knowledge on the size of the node and the filling of nodes can also be instructive. The particles so directed to the lymph nodes in diagnostic applications will contain suitable contrast or imaging agents such as ferromagnetic materials such as iron oxide, perfluorochemicals such as perfluorooctylbromide, dyes, or gamma emitting radiolabels such as Technetium-99m, Indium-111, Gallium-67, Thallium-201, Iodine-123, 125, or 131, positron emitting radiolabels such as Fluorine-18.

(2) Radiation Therapy. The use of radionuclide labeled colloids such as Gold-198 and Yttrium-90. This includes colloids with radiosensitizers, radioprotectors, or photodynamic agents. See, for example, Coleman, *Int J Radiation Onc,* 42(4):781–783, 1998, incorporated herein in its entirety by reference. These could also include neutron capturing agents such as Boron-10. These agents are activated after irradiation with neutrons. See Barth et al, *Cancer Res* 50:1061–1071, 1990, incorporated herein in its entirety by reference.

(3) The Delivery of Therapeutic Agents to Lymph Nodes. Agents and diseases relevant in this regard include antigens (vaccines), DNA, RNA, peptides, biological response modifiers, antimicrobial agents for treatment of infection of the nodes such as in filariasis, brucellosis, tuberculosis, HIV, and antitumour agents such as mitomycin C, bleomycin, etc. See, for example, Kohno et al., *J Infect Chemother,* 4:159–173, 1998; Lasic et al., in *Vesicles,* Rosoff (ed), Marcel Dekker, New York, 477–489, 1996; Bookman, *Curr Opin Oncol* 7(5):478–484, 1995; Alving, *J Immuno Methods,* 140:1–13, 1991; Daemen, in *Medical Applications of Liposomes,* Lasic and Papahadjopoulos (eds), Elsevier Science B.V., 117–143, 1998, Gregoriadis et al., in *Medical Applications of Liposomes,* Lasic and Papahadjopoulos (eds), Elsevier Science B.V., 61–73, 1998; and Woodle et al., in *Medical Applications of Liposomes,* Lasic and Papahadjopoulos (eds), Elsevier Science B.V., 429–449, 1998, all of which are incorporated herein in their entirety by reference. Targeted therapeutic agent delivery and retention methods are particularly important where the toxicity of the therapeutic agent is an issue. The methods of the present invention are directed to minimizing toxic side effects, lowering the required dosage amounts, and decreasing costs for the patient.

The compositions of the present invention may be administered by standard methods and particularly by subcutaneous or intracavitary injection. The compositions should satisfy the usual requirements for injection and are therefore administered in sterile, non-pyrogenic solutions such as saline. Single or multiple injections can be used for administration of the compositions. The dose administered and the volume of solution injected depends on the anatomical area to be treated or investigated.

EXAMPLES

The following examples are included to demonstrate preferred embodiments of the invention. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Colloids

Colloidal particles can have an important role in characterizing the properties of the lymphatic system as well as a possible role in delivering active agents to the lymphatic system. In this regard, a wide range of materials has been examined to include solid particles, emulsions and vesicles (liposomes). The distribution of colloidal agents depends strongly on their particle size; for example, colloids suggested for lymphoscintigraphy were found to have a median size of about 40–60 nm. Uptake into regional lymph nodes after, for example, subcutaneous administration is generally quite small. See, for example, Strand, *Crit Rev Ther Drug Carrier Syst* 6(3):211–238, 1989; Oussoren et al., *Biochim Biophys Acta* 1328:261–272, 1997; Oussoren et al., *Pharmaceutical Res,* 14(10):1479–1484, 1997; and Moghimi et al., *Prog Biophys Molec Biol* 65:221–249, 1996, all of which are incorporated herein in their entirety by reference.

Those of skill in the art will recognize that there are a variety of colloids that will be useful in the present invention. Colloidal particles suitable for use in the present invention include microspheres and nanoparticles, starburst dendrimers (see Wilbur et al., *Bioconjug Chem* 9:813–825, 1998, incorporated herein in its entirety by reference), microcapsules or nanocapsules, emulsions, microemulsions, liposomes and mimics of lipoproteins and chylomicrons. Suitable materials for producing these include polylactic acid and polyglycolic acid and their mixtures, polyactidecoglycolide mixtures, polymalic acid, polyalkylcyanoacrylates, polyanhydrides, polycaprolactones, polyphosphazenes, natural materials such as hyaluronic acid, albumin, dextran, gelatin, starch, collagen, polysaccharides and derivatives thereof and vegetable oils such as soybean oil. Particular success has been achieved with semi-synthetic phospholipids and cholesterol.

Upon formulation, solutions containing the colloids of the present invention will be administered in a manner compatible with the dosage formulation and in such amount as is effective for detection and therapeutic purposes. The formulations are administered in the form of injectable solutions.

For subcutaneous or intracavitary administration in an aqueous solution, for example, the solution should be suitably buffered if necessary and the liquid diluent first rendered isotonic with sufficient saline or glucose. These particular aqueous solutions are especially suitable for interstitial, subcutaneous, and intraperitoneal administration. In this connection, sterile aqueous media which can be employed will be known to those of skill in the art in light of the present disclosure. Some variation in dosage will necessarily occur depending on the lymph node(s) targeted. The person responsible for administration will, in any event, determine the appropriate dose for the individual subject. Moreover, for human administration, preparations should meet sterility, pyrogenicity, general safety and purity standards as required by FDA Office of Biologics standards.

Example 2

Liposomes

In a particular embodiment of the invention, the active agent may be incorporated in a liposome or conjugated to the surface of the liposome. Liposomes are lipid bilayer structures that may be formed on addition of an aqueous solution to lipids. Liposomes can and do take on a variety of shapes and sizes, both spherical and non-spherical, including but not limited to distorted, flattened or "collapsed" shapes, and even broken or fragmented shapes. They may be vesicular structures characterized by a phospholipid bilayer membrane and an inner aqueous medium. Multilamellar liposomes may have multiple lipid layers separated by aqueous medium. They form spontaneously when phospholipids are suspended in an excess of aqueous solution. The lipid components undergo self-rearrangement before the formation of closed structures and entrap aqueous solution between the lipid bilayers.

Liposomes have been described as potential agents for targeting delivery of diagnostic or therapeutic agents to a wide range of organ systems and diseases. Such targeting is due primarily to a physical feature of the liposome, such as size, charge, and lipid composition, and is not due to specific site-directed targeting. Phillips et al., in *Handbook of Targeted Delivery of Imaging Agents*, CRC Press, 149–173, 1995, incorporated herein in its entirety by reference.

Suitable liposome systems can be prepared with a mixture of phospholipids and cholesterol. The molar ratio can be varied for the desired composition. Polyethyleneglycol-phosphatidylethanolamine is an example of a modified phospholipid that can be used to provide liposomes with appropriate surface characteristics.

The preparation of liposomes is well described in the literature (see, for example, Litzinger et al., *Biochim Biophys Acta*. 1127(3):249–254, 1992; New, in *Liposomes: A Practical Approach*, New (ed), Oxford University Press, NY, 33–104, 1990). The mixture of phospholipid and cholesterol is dissolved in chloroform, placed in a round bottom glass tube, and the organic solvent is evaporated under vacuum. The lipid film so obtained is suspended by the addition of buffer to form multilamellar liposomes. Sonication, homogenization, microfluidization, dialysis, or passage of these liposomes through nucleopore filters results in the formation of small unilameller vesicles.

The materials which may be utilized in preparing liposomes for use in the present invention include any of the materials or combinations thereof known to those skilled in the art as suitable for liposome preparation. The lipids used may be of either natural or synthetic origin. The particular lipids are chosen to optimize the desired properties. Lipids which may be used to create liposome microspheres include but are not limited to: lipids such as fatty acids, lysolipids, phosphatidylcholine with both saturated and unsaturated lipids including dioleoylphosphatidylcholine; dimyristoylphosphatidyl-choline; dipentadecanoylphosphatidylcholine, dilauroylphosphatidylcholine, dipalmitoyl-phosphatidylcholine; distearoylphosphatidylcholine; phosphatidylethanolamines such as dioleoylphosphatidylethanolamine; phosphatidylserine; phosphatidylglycerol; phospha-tidylinositol, sphingolipids such as sphingomyelin; glycolipids such as ganglioside GM1 and GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids; diacetyl phosphate; stearylamine; cardiolipin; phospholipids with short chain fatty acids of 6–8 carbons in length; synthetic phospholipids with asymmetric acyl chains (e.g., with one acyl chain of 6 carbons and another acyl chain of 12 carbons); 6-(5-cholesten-3-β-yloxy)-1-thio-β-D-galactopyranoside; digalactosyldiglyceride; 6-(5-cholesten-3-β-yloxy)hexyl-6-amino-6-deoxy-1-thio-β-D-galactopyranoside; 6-(5-cholesten-3-β-yloxy)hexyl-6-amino-6-deoxyl-1-thio-α-D-mannopyranoside; 12-(((7'-diethylaminocoumarin-3-yl)carbonyl)methyl-amino) octadecanoic acid; N-12-(((7'-diethylaminocoumarin-3-yl) carbonyl)methyl-amino)octadecanoyl-2-aminopalmitic acid; cholesteryl-(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinyl-glycerol; 1-hexadecyl-2-palmitoyl-glycerophosphoethanolamine; palmitoylhomocysteine, and/or combinations thereof.

If desired, a variety of cationic lipids such as DOTMA, N-1-(2,3-dioleoyloxy)propyl-N,N,N-trimethylammonium chloride; DOTAP, 1,2-dioleoyloxy-3-(trimethylammonio) propane; and DOTB, 1,2-dioleoyl-3-(4'-trimethyl-ammonio) butanoyl -sn-glycerol may be used. In general the molar ratio of cationic lipid to non-cationic lipid in the liposome may be, for example, 1:1000, 1:100, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid when cationic lipid is used to construct the microsphere. Preferably, this non-cationic lipid is dipalmitoylphosphatidylcholine, dipalmitoylphosphatidylethanolamine or dioleoylphosphatidylethanolamine. In lieu of cationic lipids as described above, lipids bearing cationic polymers such as polylysine or polyarginine may also be used to construct the microspheres and afford binding of a negatively charged therapeutic, such as genetic material, to the outside of the microspheres.

Other useful lipids or combinations thereof apparent to those skilled in the art which are in keeping with the spirit of the present invention are also encompassed by the present invention. For example, carbohydrate-bearing lipids may be employed for in vivo targeting, as described in U.S. Pat. No. 4,310,505, the disclosures of which is hereby incorporated herein by reference, in its entirety.

The most preferred lipids are phospholipids, preferably DPPC and DSPC, and most preferably DSPC. It is also preferable to include cholesterol in the lipid formulation.

The size of active agent-containing liposomes can be adjusted, if desired, by a variety of procedures including extrusion, filtration, sonication, homogenization, employing a laminar stream of a core of liquid introduced into an immiscible sheath of liquid, extrusion under pressure through pores of defined size, and similar methods, in order to modulate resultant liposomal biodistribution and clearance. The foregoing techniques, as well as others, are discussed, for example, in Mayer et al., *Biochim Biophys Acta,* 858:161–168, 1986; Hope et al., *Biochim Biophys Acta,* 812:55–65, 1985; Mayhew et al., *Methods in Enzymology,* 149:64–77, 1987. The disclosures of the foregoing publications are incorporated by reference herein, in their entirety.

Example 3

The Biotin/Avidin System

The ability to target specific lymph nodes for detection, diagnosis and/or therapy is highly desirable. The biotin/avidin system can be used in methods for targeting lymph nodes. Avidin is a glycoprotein, found in egg whites, that has an extremely high binding affinity for biotin, a natural B-complex vitamin found in every living cell. Streptavidin, derived from *Streptomyces avidinii*, is similar to avidin in its chemical and physical characteristics and identical to avidin in its ability to bind biotin. Both avidin and streptavidin have a tetravalency for biotin. Streptavidin can be used in place of avidin in many applications because of its low nonspecific tissue binding property. Both avidin and streptavidin have a tetravalency for biotin, thus permitting amplification when the former bind to biotin. The present invention encompasses natural avidin and its derivatives and analogs capable of being bound by biotin, in particular, avidin modified to have lower immunogenicity.

Natural biotin is a water-soluble vitamin found in every living cell. The present invention encompasses natural biotin and its derivatives and analogs capable of being bound by avidin. Exemplary biotin molecules include 2'-thiobiotin; 2'-iminobiotin; 1'-N-methoxycarbonylbiotin; 3'-N-methoxycarbonylbiotin; 1-oxybiotin; 1-oxy-2'-thiobiotin; 1-oxy-2'-iminobiotin; 1-sulfoxidebiotin; 1-sulfoxide-2'-thiobiotin; 1-sulfoxide-2'-iminobiotin; 1-sulfonebiotin; 1-sulfone-2'-thiobiotin; 1-sulfone-2'-iminobiot imidazolidone derivatives such as desthiobiotin (d and dl optical isomers), dl-desthiobiotin methyl ester, dl-desthiobiotinol, D-4-n-hexylimidazolidone, L-4-nhexylimidazolidone, dl-4-n-butylimidazolidone, dl-4-n-propylimidazolidone, dl-4-ethylimidazolidone, dl-4-methylimidazolidone, imidazolidone, dl-4,5-dimethylimidazolidone, meso-4,5-dimethylimidazolidone, dl-norleucine hydantoin, D-4n-bexyl-2-thionoimidazolidine, d-4-n-hexyl-2-iminoimidazolidine and the like; oxazolidone derivatives such as D-4-n-hexyloxazolidone, D-5-n-hexyloxazolidone and the like; [5-(3,4-diaminothiophan-2-yl] pentanoic acid; lipoic acid; 4-hydroxyazobenzene-2'-carboxylic acid; and the like. Preferred biotin molecules for use in the practice of the present invention are natural biotin conjugated to the headgroup region of a phospholipid. These exemplary biotin molecules may be produced substantially in accordance with known procedures therefore. Conjugation of the exemplary biotin molecules to colloids proceeds substantially in accordance with known procedures therefore and with procedures described herein with regard to biotin conjugation.

Example 4

Other Ligand/Anti-Ligand Systems

In addition to biotin/avidin, other ligand/anti-ligand systems useful in the present invention include synthetically designed ligand/anti-ligand pairs with high affinity based on polyvalency. For example, Rao et al. described one pair with higher affinity than biotin/avidin using tris vancomycin carboxamide for binding to the trivalent ligand derived from D-Ala-D-Ala (Rao et al., *Science,* 280(5364):708–711, 1999, incorporated herein in its entirety by reference).

Another substitution includes antibody/antigen pairs. For example, the biotin ligand on the surface of the colloid could be replaced by an antigen. In the presence of the corresponding antibody anti-ligand, an aggregate complex could form. Likewise, of the antibody/antigen pair, the antibody could serve as the ligand and be associated with the surface of the colloid while the corresponding antigen could serve as the anti-ligand (Leserman et al., in *Liposomes From Biophysics to Therapeutics,* Ostro (ed), Marcel Dekker, New York, pp. 157–194, 1987; Kung et al., *Biochim Biophys Acta* 839: 105–109, 1985; and Hermanson, *Bioconjugate Techniques,* Academic Press, San Diego, Calif., pp. 552–553, 1996, all of which are incorporated herein in their entirety by reference). Completely synthetic antibody-like molecules termed "peptabodies" could substitute for the antibody in the antibody/antigen pair and be used in conjunction with a corresponding molecule recognized by the peptabody in this procedure. (Terskikh et al., *Proc Natl Acad Sci USA* 94: 1663–1668, 1997, incorporated in its entirety by reference).

Another example of an alternate ligand/anti-ligand pair is lectin/complementary carbohydrate. For example, lectin could serve as the ligand. Lectins on the surface of a colloid could aggregate after association with the complementary carbohydrate anti-ligand (Leserman et al., in *Liposomes From Biophysics to Therapeutics*, Ostro (ed) Marcel Dekker, New York, pp. 157–194, 1987; and Hermanson, *Bioconjugate Techniques*, Academic Press, San Diego, Calif., pp. 548–549, 1996, incorporated in their entirety by reference). Likewise, of the lectin/complementary carbohydrate pair, the lectin could serve as the anti-ligand.

Other ligand/anti-ligand pairs such as the folate/folate receptor, fibrin/plasminogen, and sialyl Lewis X/E-selectin could potentially replace biotin/avidin as the ligand/anti-ligand pair (Gabizon et al., *Bioconjugate Chem* 10:289–298, 1999; Heeremans et al., *Thromb Haemost* 75(1):134–139, 1996; DeFrees et al., *J Am Chem Soc* 118:6101–6104, 1996, all of which are incorporated in their entirety by reference).

Example 5

Kits for Detection and Therapy of Lymph Nodes

Kits comprising (1) ligand conjugated to a colloid containing an active agent, and (2) anti-ligand with or without an active agent comprise another aspect of the present invention. The detection/therapeutic kits comprising the active agents disclosed herein will generally contain, in suitable container means, a detection- or therapeutically-effective amount of an active agent. The kit may have a single container means that contains the ligand-targeting colloid-active agent, or it may have distinct container means for each compound.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

When the components of the kit are provided in one or more liquid solutions, the liquid solution is an aqueous solution, with a sterile aqueous solution being particularly preferred. The ligand-colloid-active agent composition and the anti-ligand-active agent composition may also be formulated into syringeable compositions. In which case, the container means may itself be a syringe, or other such like apparatus, from which the formulation may be administered into the body, preferably by injection or even mixed with the other components of the kit prior to injection. Dosage of each of the compositions will vary from subject to subject depending upon the use of the compositions, size of the subject, potential location of the lymph node to be targeted, body weight of the subject, etc. The calculation and adjustment of dosages of a variety of compositions is well-known to those of skill in the art.

In an alternate embodiment, components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the ligand-colloid-active agent compositions may be placed, preferably, suitably allocated. The kit will also generally contain a second vial or other container into which the anti-ligand-active agent compositions may be placed. The kits may also comprise a second/third container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained. Alternatively, the vials may be prepared in such a way as to permit direct introduction of the composition into an intravenous drug delivery system.

Irrespective of the number or type of containers, the kits of the invention may also comprise, or be packaged with, an instrument for assisting with the injection/administration or placement of the compositions of the invention within the body of a mammal. Such an instrument may be a syringe, pipette, forceps, measured spoon, eye dropper or any such medically approved delivery vehicle.

Example 6

Detection/Therapeutic Agents

The detection/therapeutic agents used in the methods of the present invention can be any or multiples of the following:

A—diagnostic or therapeutic agents (e.g., alpha-, beta-, gamma-, positron-, x-ray- and fluorescence-emitters; electron- and neutron-capturing agents, paramagnetic and ferromagnetic agents);
B—photoactivated dyes for detection or therapy;
C—cytotoxic agents (e.g., drugs, toxins, hormones, cytokines, hormone antagonists, receptor antagonists);
D—biological response modifier agents (e.g., vitamins, cytokines, autocrines, peptides, anti-angiogenesis agents, certain hormones and drugs);
E—dyes for visual detection;
F—radiosensitizers and radioprotectors;
G—DNA, RNA; and
H—antigens for vaccines.

Among the detection and therapeutic agents useful in the methods of the present invention, gamma-emitters, positron-emitters, x-ray emitter, paramagnetic or ferromagnetic ions, and fluorescence-emitters are suitable for detection and/or therapy, while beta- and alpha-emitters and neutron-capturing agents can be used for therapy.

Therapeutic Agents

Any of a variety of therapeutics may be encapsulated in the colloids or conjugated to the surface of the colloids. Many pharmaceutical compositions are known which have cytotoxic effects on cells. They are to be found in compendia of drugs, such as the Merck Index, Goodman and Gilman, and the like, and in the references cited above. Any such pharmaceutical composition can be conjugated to anti-ligand or loaded into the ligand-colloid by conventional means well known in the art.

Preferred therapeutic agents suitable for use herein include conventional chemotherapeutics, such as vinblastine, doxorubicin, bleomycin, methotrexate, 5-fluorouracil, 6-thioguanine, cytarabine, cyclophosphamide and cisplatinum, as well as other conventional chemotherapeutics as described in DeVita et al., *Cancer: Principles and Practice of Oncology, 5th ed.*, J. B. Lippincott Co., Philadelphia, Pa., Chapter 19, 375–512, 1997, incorporated herein by reference. The preferred therapeutic agent for use in the present invention will depend on the particular tumor or type of lesion to be treated.

Examples of known cytotoxic agents useful in the present invention are listed in Goodman et al., *The Pharmacological Basis of Therapeutics, 6th Ed.*, Gilman et al., (eds.), Macmillan Publishing Co., New York, 1980, incorporated herein in its entirety by reference. These include taxol; nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; antibiotics; anti-virals; vaccines; and photodynamic dyes.

Examples of known hormone suppressants useful in the present invention are listed in Goodman et al, *The Pharmacological Basis of Therapeutics, 6th Ed*, Gilman et al. (eds), Macmillan Publishing Co. New York, 1980. These include adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), anti-estrogens (tamoxifen), and androgens (testosterone propionate and fluoxymesterone).

Drugs that interfere with intracellular protein synthesis can also be used in the methods of the present invention; such drugs are known to those skilled in the art and include puromycin, cycloheximide, and ribonuclease.

If desired, more than one therapeutic may be delivered using the colloid. For example, a single colloid may contain more than one therapeutic or colloid containing different therapeutics may be co-administered. By way of example, a therapeutic radionuclide such as Yttrium-90 and chemotherapeutic agent such as vincristine may be administered at the same time.

Similarly, prodrugs may be encapsulated in the colloids, and are included within the ambit of the term therapeutic, as used herein. Prodrugs are well known in the art and include inactive drug precursors which, when exposed to high temperature, metabolizing enzymes, cavitation and/or pressure, in the presence of oxygen or otherwise, or when released from the colloid, will form active drugs. Such prodrugs can be activated in the method of the invention, upon the application of ultrasound to the prodrug-containing colloid with the resultant cavitation, heating, pressure, and/or release from the colloid. Suitable prodrugs will be apparent to those skilled in the art, and are described, for example, in Sinkula et al., *J Pharm Sci* 64:181–210, 1975, the disclosure of which is hereby incorporated herein by reference in its entirety.

Radioisotopes may also be used as therapeutic agents. Any conventional method of radiolabeling which is suitable for labeling isotopes for in vivo use will be generally suitable for labeling therapeutic agents according to the present invention.

Isotopes preferred for therapeutic use include: Actinium-225, Bismuth-212, Lead-212, Bismuth-213, Iodine-125, Iodine-131, Rhenium-186, Rhenium-188, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, and Gold-199.

Detection Agents

Detection agents of use in the present invention include radioisotopes and dyes. Any conventional method of radiolabeling which is suitable for labeling isotopes for in vivo use will be generally suitable for labeling detection agents according to the present invention. Internal detection procedures include intraoperative, intravascular or endoscopic, including laproscopic, techniques, both surgically invasive and noninvasive.

When detecting a lymph node, a high signal-to-background ratio needs to be achieved. Therapy also requires a high absolute accretion of the therapeutic agent in the lymph node, as well as a reasonably long duration of uptake and binding.

Suitable radioisotopes for the methods of the present invention include: Actinium-225, Astatine-211, Iodine-123, Iodine-125, Iodine-126, Iodine-131, Iodine-133, Bismuth-212, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-186, Rhenium-188, Tellurium-121m, Tellurium-122m, Tellurium-125m, Thulium-165, Thulium-167, Thulium-168, Technetium-99m, Fluorine-18, Silver-111, Platinum-197, Palladium-109, Copper-67, Phosphorus-32, Phosphorus-33, Yttrium-90, Scandium-47, Samarium-153, Lutetium-177, Rhodium-105, Praseodymium-142, Praseodymium-143, Terbium-161, Holmium-166, Gold-199, Cobalt-57, Cobalt-58, Chromium-51, Iron-59, Selenium-75, Thallium-201, and Ytterbium-169. The most preferred radioisotope for use in the current invention is Technetium-99m. Preferably the radioisotope will emit a particle or ray in the 10–7,000 keV range, more preferably in the 50–1,500 keV range, and most preferably in the 80–250 keV range.

Isotopes preferred for external imaging include: Iodine-123, Iodine-131, Indium-111, Gallium-67, Ruthenium-97, Technetium-99m, Cobalt-57, Cobalt-58, Chromium-51, Iron-59, Selenium-75, Thallium-201, and Ytterbium-169. Technetium-99m is the most preferred radioisotope for external imaging in the present invention.

Isotopes most preferred for internal detection include: Iodine-125, Iodine-123, Iodine-131, Indium-111, Technetium-99m and Gallium-67. Technetium-99m is the most preferred isotope for internal detection.

Dyes may also be used as detection agents. In order to aid with localization of the sentinel lymph node for a tumor, blue dye has been injected around the tumor. The blue dye travels into the lymphatic system and through the sentinel lymph node. While this permits visualization of lymph nodes, for example, during surgical procedures, it does not permit detection of the sentinel lymph node because the blue dye does not localize at the first lymph node encountered, but passes on to lymph nodes further along the lymph node chain.

Incorporation of blue dye with the colloid of the aggregated colloid complex of the present invention provides for retention of the blue dye at the first lymph node encountered, or in the chain of draining lymph nodes, depending upon the timing of administration of the anti-ligand-active agent.

Example 7

Methods for Preparing Ligand-Colloid Conjugates

Methods for preparing conjugates of ligand, such as biotin, with colloid are known to those skilled in the art. See, for example, Schuber, in *Liposomes as Tools in Basic Research and Industry*, Philippot and Schuber (eds), CRC Press, Boca Raton, 21–39, 1995, incorporated herein in its entirety by reference. A preferred method is described below.

Liposomes were comprised of distearoyl phosphatidylcholine (DSPC) (Avanti) Polar Lipids, Pelham, Ala.); cholesterol (Chol) (Calbiochem, San Diego, Calif.); Nbiotinoyl distearoyl phosphoethanolamine (Biotin-DSPE) (Northern Lipids, Vancouver, Canada); and α-tocopherol (Aldrich, Milwaukee, Wis.). All lipids were used without further purification. The lipids were mixed in chloroform at a total molar ratio of 58:39:1:2 (DSPC:Chol:Biotin-DSPE:α-tocopherol). Chloroform was then removed by rotary evaporation to form a lipid film. The lipid film was stored overnight in a vacuum desiccator to remove organic solvent. Samples were rehydrated with 300 mM sucrose (Sigma, St. Louis, Mo.) in sterile water for injection and warmed to 55° C. for 15 min with periodic vortexing until all of the lipids were in suspension. The resultant multilamellar vesicles formed from rehydration were then frozen in liquid nitrogen and lyophilized. The resultant dry sugar-lipid preparations were then rehydrated with 200 mM reduced glutathione (GSH) (Sigma, St. Louis, Mo.) in Dulbeccco's phosphate buffered saline pH 6.3 at a lipid concentration of 102 mM. The GSH-lipid suspension was warmed to 55° C. for 10 min. For some preparations, the suspension was allowed to cool to room temperature and then stored overnight in the refrigerator. The solutions were then diluted at a volume/volume ratio of 1 part lipid suspension to 2 parts Dulbecco's phosphate buffered saline containing 100 mM GSH and 150 mM sucrose. The diluted lipid suspensions were then extruded through a series (2 passes, 2μ; 2 passes, 400 nm; 5 passes, 100 nm) of polycarbonate filters (Lipex Extruder, Vancouver, Canada) at 55° C. The extruded lipid solution was then washed in Dulbecco's phosphate buffered saline containing 75 mM sucrose and centrifuged at 200,000× g for 45 min to remove unencapsulated GSH and sucrose, and to concentrate the liposome sample. The washing step was repeated 3 times. The final liposome pellet was resuspended in Dulbecco's phosphate buffered saline pH 6.3 containing 300 mM sucrose at a lipid concentration of 102 mM and stored in the refrigerator at 4° C.

Example 8

Methods for Preparing Biotin-Colloid Conjugates Encapsulating Blue Dye

Methods for preparing biotin-colloid conjugates encapsulating blue dye are known to those skilled in the art. A preferred method is described below.

Liposomes encapsulating blue dye were comprised of the same lipids as for the biotin-liposomes. The liposomes were processed in an identical fashion as listed above except patent blue violet dye (Sigma, St Louis, Mo.; CI 42045) was included during processing in the following manner: 1). The dry sugar-lipid preparation was rehydrated with Dulbeccco's phosphate buffered saline pH 6.3 containing 200 mM GSH and 10 mg/ml of blue dye at a lipid concentration of 102 mM. 2) Immediately before extrusion, the liposome solution was diluted at a volume/volume ratio of 1 part lipid suspension to 2 parts Dulbecco's phosphate buffered saline containing 100 mM GSH, 150 mM sucrose and 10 mg/ml of blue dye.

Example 9

Methods for Radiolabeling Ligand-Colloid Conjugates Alone or Encapsulating Blue Dye Methods for radiolabeling ligand-colloid conjugates, such as biotin-colloid conjugates, which may encapsulate blue dye, are known to those skilled in the art. A preferred method is described below.

The Technetium-99m ($^{99m}$Tc) carrier found most preferable is an alkylenepropyleneamine oxime that complexes with $^{99m}$Tc and can be purchased as a lyophilized preparation (Ceretec™, Nycomed-Amersham, Arlington Hgts, Ill.). In this form, HMPAO is mixed with sterile eluate from a $^{99m}$Tc-generator The generator eluate may be adjusted to a radioactive concentration of between 037–1.11 GBq (10–30 mCi) in 5 ml by dilution with preservative free, nonbacteriostatic saline prior to mixing with 0.5 mg of HMPAO. The $^{99m}$Tc complex forms almost immediately and is incubated for 5 min at room temperature. This mixture of $^{99m}$Tc-HMPAO (0.5 ml, 1 mCi) was then incubated with 1 ml (102 mM of lipid) of either biotin-liposomes containing GSH alone or biotin-liposomes coencapsulating GSH and blue dye prepared as described above. The $^{99m}$Tc-HMPAO-liposome mixture was incubated for 15–30 min at room temperature with intermittent swirling. The radiolabeled liposomes were then separated from any free $^{99m}$Tc by passage over a Sephadex G-25 column (PD10 column, Pharmacia Biotech, Uppsala, Sweden) equilibrated with Dulbecco's phosphate buffered saline pH 6.3. Labeling efficiencies were checked by determining the activity before and after column separation of the $^{99m}$Tc-biotin-liposomes using a dose calibrator (Radix, Houston, Tex.). Labeling efficiencies averaged 97% for biotin-liposomes containing GSH and 92% for biotin-liposomes coencapsulating GSH and blue dye. Postcolumn preparations of the $^{99m}$Tc-biotin-liposomes were used immediately for injection.

Example 10

Methods for Preparing Anti-Ligand-Active Agent Compositions

Methods of preparing anti-ligand-active agent compositions are known in the art with commonly used avidin-active agents reviewed by Bayer and Wilchek (Bayer et al., *Meth Enzymol* 184:174–187, 1990, incorporated in its entirety by reference). This review article includes methods for covalently conjugating fluorescent agents (fluorescein isothiocyanate), radiolabels (tritium), proteins (ferritin), enzymes (penicillinase), and toxins (ricin A). Several of these avidin-active agents are commercially available (Sigma catalog, St. Louis, Mo.). Examples of avidin-active agents for therapy include a) the chemotherapeutic agent cisdiamminedichloroplatinum (II) complexed to a carboxymethyl dextran-avidin conjugate; and b) boron-10 chlorpromazine conjugated to avidin for use in boron neutron capture therapy (Schechter et al., *In J Cancer* 48(2):167–172, 1991 and Komura et al., *Melanoma Research* 1:397–403, 1992, incorporated in their entirety by reference). Other reported uses of avidin-active agents include using a monoclonal antibody-avidin conjugate to increase delivery of therapeutic agents through the blood brain barrier; and b) delivery of a luteinizing hormone releasing hormone-avidin conjugate for improved antibody titer to luteinizing hormone releasing hormone for disruption of reproductive function (Kang et al., *J Pharm Exptl Ther* 269: 344–350, 1994 and Tiong et al., *Vaccine* 11:425–430, 1993, incorporated in their entirety by reference).

When the active agent is a radioisotope for detection or therapy, the preferred method of preparation will depend, for example, on the isotope chemistry. Methods for conjugating anti-ligand, for example, avidin, to a detection or therapeutic agent include the following: (a) the chloramine-T or Bolton-Hunter procedures for conjugating iodine, (b) the procedures described by Griffiths et al., *Cancer Res* 51(17):4594–4602, 1991, or Fritzberg et al., U.S. Pat. No. 5,120,526, to conjugate Technetium or Rhenium (c) through bifunctional chelating agents as described by Meares et al., *Br J Cancer Suppl* 10:21–26, 1990, to conjugate metallic nuclides. Additionally, avidin can be bound to dendrimers by procedures described for amino-containing proteins as described by Hnatowich et al., *J Nucl Med* 28(8):1294–1302, 1987. The disclosures of the above publications are incorporated herein in their entirety by reference.

Example 11

Methods for Detecting Lymph Nodes

Gamma Scintigraphy

An application for the method of the present invention is for gamma scintigraphy. In this case, for example, a suitably radiolabeled conjugate is administered with the intention of obtaining an image of the lesion.

The method of the invention can be practiced either with scintigraphic or magnetic resonance imaging agents. A combination of these imaging agents can also be used, although this requires more complex instrumentation and data processing.

Scintigraphic imaging according to the method of the invention is effected by obtaining a scintigram of the lesion of interest.

The scintigram is normally taken by a gamma imaging camera having one or more windows for detection of energies in the 50–600 keV range. Use of radioisotopes with higher energy, beta, or positron emissions would entail use of imaging cameras with the appropriate detectors, all of which are conventional in the art.

The scintigraphic data can be stored in a computer for later processing.

Methods useful for internal detection and/or treatment of lymph nodes are disclosed in Tiourina et al., *Eur J Nucl Med* 25:1224–1231, 1998; Reintgen, *J Nucl Med* 39(12) 22N–36N, 1998; DeCicco et al., *J Nucl Med* 39(12):2080–2084, 1998; and Hader et al., *AORN J* 68(4): 572–588, 1998, the disclosures of which are incorporated herein in their entirety by reference. The methods of the present invention can be used to enhance the methods disclosed in these references.

Magnetic Resonance Imaging

Magnetic resonance imaging (MRI) is effected in an analogous manner to scintigraphic imaging except that the imaging agents will contain magnetic resonance (MR) enhancing species rather than radioisotopes. It will be appreciated that the magnetic resonance phenomenon operates on a different principle from scintigraphy. Normally, the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/ or various other strongly $T_1$-dependent or $T_2$-dependent imaging techniques, and the composition of the medium in which the agent is dissolved or suspended. These factors, and their relative importance are known in the art. See, e.g., Okuhata, *Adv Drug Delivery Rev* 37:121–137, 1999; Pykett, *Sci Am*, 246(5):78–88, 1982; Runge et al., *Am J Roentgeno*, 141(6):1209–1215, 1983, all of which are incorporated herein in their entirety by reference.

The MR image enhancing agent must be present in sufficient amounts to enable detection by an external camera, using magnetic field strengths which are reasonably attainable and compatible with patient safety and instrumental design. The requirements for such agents are well known in the art.

MRI contrast agents are well known in the art and include, for example, Gadolinium, Iron, Manganese, Rhenium, Europium, Lanthanium, Holmium, and Terbium.

The MR scans are stored in a computer and the images processed analogously to the scintigraphic data.

X-Ray and Computerized Axial Tomography (CT) Imaging

X-ray and Computerized Axial Tomography (CT) are both based on using an X-ray beam. CT imaging allows for 3 dimensional pictures by backprojection reconstruction of images obtain in radial fashion around a patient Contrast for both plain X-ray and CT imaging is effected in a manner analogous to that described for scintigraphic and MRI imaging except that the imaging agents provide contrast by increasing the attenuation of the X-ray beam. Attenuation of the X-ray beam depends on the energy of the beam and the tissue mass attenuation coefficient. The greater the average proton number Z of the tissue, the greater the attenuation. CT and X-ray contrast imaging agents are therefore based on high Z atoms such as iodine. Several colloid based iodine containing agents have been under development including liposomes encapsulated with iodine. Since the resolution of CT and X-ray imaging is greater than that of scintigraphy, colloidal imaging agents that target the lymph node could provide high resolution contrast of the interior of a lymph node. Factors associated with ideal X-ray and CT imaging contrast agents are well known in the art. See Krause, *Adv Drug Deliv Rev*, 37:159–173, 1999, incorporated in its entirety by reference.

Ultrasound Imaging

The use of ultrasound as a diagnostic imaging modality has increased in recent years. Ultrasound imaging can be enhanced by the use of ultrasound imaging agents. The agents increase contrast by reflecting and scattering ultrasound waves. The use of ultrasound contrast can increase delineation of important structures in the body and increase diagnostic ability. Much recent effort has been dedicated to the targeting of ultrasound contrast colloidal to tissues of interest in the body. Common ultrasound contrast colloids include air microbubbles coated with protein and liposomes which encapsulate air. Factors affecting the quality of ultrasound contrast are well known. See Klibanov, *Adv Drug Deliv Rev*, 37:139–157, 1999, incorporated in its entirety by reference.

Neutron Capture Therapy

Neutron capture therapy consists of administration of a nonradioactive isotope which can be split into a heavy ion and an alpha particle upon irradiation with thermal neutrons. The advantage of this system is that the therapeutic radiation can be better controlled and only the site irradiated with the thermal neutrons and containing the neutron capture agent will receive a high dose of radiation. The most commonly used isotope for this therapy is boron-10. The delivery of boron-10 to specific sites in the body using colloids has been under development. One proposed system uses boron-10 encapsulated in a liposome. (See, for example, Johnsson et al., *J Liposome Res*, 9:53–79, 1999; Rawls, *C&EN*, 26–29, Mar. 22, 1999; and Barth et al., *Cancer Res*, 50:1061–1070, 1990, incorporated in their entirety by reference.) This use of the lymph node delivery system with BCNT would have advantages to one skilled in the art because the site of initial subcutaneous injection would not receive any radiation while the site of uptake in the lymph node could receive the targeted radiation therapy.

Vaccine Antigen Delivery

Vaccine adjuvants are agents when given in combination with an antigen, greatly increase the immune response to the antigen. Vaccine adjuvants are essentially antigen delivery systems, however, the mechanisms and locations involved in the delivery of the antigen are poorly understood. Most common adjuvants are colloids. Typical colloids used are aluminum hydroxide colloids and liposome colloids. (See *Theory and Practical Application of Adjuvants*. Stewart-Tull (ed), John Wiley & Sons Ltd., Chichester, England, 1995, incorporated herein by reference.) The most recent information indicates that antigen delivery to the lymph node and induction of lymph node hypercellularity are important aspects of adjuvant function. Lindblad, in *Theory and Practical Application of Adjuvants*, Stewart-Tull (ed), John Wiley & Sons Ltd., Chichester, England, pg. 21–35, 1995 and Gregoriadis, in *Theory and Practical Application of Adjuvants*, Stewart-Tull (ed), John Wiley & Sons Ltd., Chichester, England, pg. 145–169, 1995, incorporated herein in their entirety by reference. Since the essential nature of how vaccine adjuvants work is poorly understood, most vaccine development is conducted by trial and error. These trial and error techniques are inefficient and costly. Much effort is currently being focused on understanding how vaccines work. This work has been spurred by the effort to develop an effective vaccine for treatment and prevention of HIV infection and as an immune stimulant for cancer therapy. Even though vaccine adjuvants are clearly antigen delivery vehicles, virtually no studies have used isotopes or imaging or other detection agents such as dyes to study their biodistribution in the body after administration. If lymph node delivery is important, it will be obvious that the colloid-ligand-anti-ligand system described herein will be very useful for enhancing immune response to an antigen which is delivered to the lymph nodes by this system.

Without further elaboration, it is believed that one skilled in the art can, using the preceding description, utilize the present invention to detect lymph nodes draining a specific site in a subject.

Example 12

Methods for Targeted Delivery and Retention of Diagnostic and Therapeutic Agents to the Sentinel Node(s)

The following standard experimental protocol was used for examples 13–16. Rabbits were anesthetized with ketamine/xylazine intramuscularly and placed in the supine position under a Picker Dyna 4 Gamma camera. Rabbits were injected subcutaneously with 0.3 ml of $^{99m}$Tc-biotin-liposomes into the dorsum of both the left and right feet. Immediately after injection, manual massage was applied to the dorsum of the foot for 5 min in order to stimulate liposome movement. At 5 min post injection, in experimental rabbits, avidin was injected subcutaneously into the foot approximately 2 cm proximal to the site of the initial liposome injection. No massage was performed over the site of avidin injection. After 30 min, leg raising was initialized for 1 min at 30, 40, 50 and 60 min after liposome injection. In the asymmetric experiments 1, 3, and 4 (Examples 13, 15, and 16 below), the avidin was injected into the right foot while the left foot served as a control. In symmetric experiment 2 (Example 14 below), the avidin was injected into both feet of the same rabbit in 4 rabbits and 4 control rabbits were administered no avidin.

Example 13

Increased Retention of Liposomes in Lymph Nodes

To demonstrate the use of biotin-colloid/avidin technology to increase the retention of the liposomes in lymph nodes, biotin-liposomes encapsulating only glutathione and labeled using the $^{99m}$Tc-HMPAO technique were studied. Four rabbits were subcutaneously injected in the foot pads of both feet with $^{99m}$Tc-biotin-liposomes in 0.3 ml volume. This is an asymmetric study, since only one foot was then subcutaneously injected with 5 mg of avidin in 0.3 ml of saline 5 min after injection of the $^{99m}$Tc-biotin-liposomes. The avidin was subcutaneously injected on the right rabbit foot 2 cm proximal from the liposome injection. Scintigraphic imaging with a gamma camera was performed of the rabbits for the first hour after liposome injection and then at 20 hours to follow the movement of the $^{99m}$Tc-biotin-liposomes in relationship to the avidin. These images are analyzed by drawing a region of interest around the site of the liposome injection and around the popliteal lymph nodes.

The rabbits were sacrificed at 20 hr and tissue samples were taken of the popliteal nodes and counted in a scintillation well counter. The percent uptake of $^{99m}$Tc-biotin-liposomes in the nodes was compared to a standard representing the total amount injected in each foot pad.

These results are shown in Table 1. There were 11.1% of the $^{99m}$Tc-biotin-liposomes retained on the right side and 1.6% retained in the left side without avidin. The difference from the control node was highly significant with p=0.017.

TABLE 1

Tissue Biodistribution Results at 20 Hours
$^{99m}$Tc-Biotin-Liposomes with Asymmetric Avidin Protocol (n = 4)

|  | % uptake | Standard Error |
|---|---|---|
| Experimental Node | 11.1* | 3.1 |
| Control Node | 1.6 | 0.2 |

From the biodistribution studies, it can be seen that the $^{99m}$Tc-biotin-liposomes are retained in high percentages in the popliteal lymph node on the side in which the avidin was injected. This demonstrates that the use of $^{99m}$Tc-biotin-liposomes with avidin results in a significantly increased retention of liposomes to the lymph nodes. These results suggest that this method could be used to increase the delivery of liposome encapsulated agents to the lymph nodes.

Example 14

Altered Total Body Distribution of Liposomes

To demonstrate that the total body distribution of $^{99m}$Tc-biotin-liposomes is changed in rabbits that were injected with avidin in both feet compared to rabbits that did not get avidin in either foot, $^{99m}$Tc-biotin-liposomes were subcutaneously injected into both foot pads and the avidin was subcutaneously injected 2 cm proximal to the liposome injection site on both feet. Four rabbits were administered avidin and 4 rabbits served as controls and received no avidin. This is a symmetric study which was compared to control rabbits in which $^{99m}$Tc-biotin-liposomes were given in both foot pads and no avidin was administered. Animals were imaged as before for the first hour after injection and at 20 hours after injection. Animals were sacrificed at 20 hours and tissue samples were obtained from the popliteal lymph nodes, iliac lymph nodes, blood, spleen and liver.

The retention in the popliteal nodes was 11.4% (left) and 16.0% (right) with avidin compared with 17% (left) and 2.6% (right) without avidin. These differences were highly significant with p=0.004 for left nodes and p=0.01 for right nodes. The iliac nodes also had increased retention in avidin rabbits compared with control rabbits. The avidin also greatly reduced the uptake of $^{99m}$Tc-biotin-liposomes by the liver and spleen. These results are depicted in Table 2.

TABLE 2

Tissue Biodistribution Results at 20 Hours
$^{99m}$Tc-Biotin-Liposomes with Symmetric Avidin Protocol (n = 4)

|  | Experimental + Avidin | SE | Control − Avidin | SE |
| --- | --- | --- | --- | --- |
| Left Popliteal Node | 11.4 | 2.0 | 1.7* | 0.8 |
| Right Popliteal Node | 15.9 | 3.5 | 2.6Δ | 1.2 |
| Iliac Node | 2.3 | 0.8 | 0.3 | 0.03 |
| Liver | 2.7 | 1.1 | 16.9† | 0.5 |
| Blood | 0.6 | 0.1 | 7.7‡ | 1.0 |
| Spleen | 0.2 | 0.06 | 0.4 | 0.03 |

*p = 0.004 left control vs. left experimental
Δp = 0.01 right control vs. right experimental
†p = 0.01
‡p = 0.04

It can be seen that the distribution is significantly different in the rabbits that received avidin compared to the control rabbits.

Example 15

Visual Marking of Sentinel Lymph Nodes with Blue Dye

Biotin-liposomes labeled with $^{99m}$Tc can encapsulate blue dye for visually marking the first lymph node encountered. The blue dye can also be considered as an example of drug delivery to a lymph node. Other drugs such as anticancer agents, antiviral agents, vaccines, photodynamic dyes, antibiotics, and therapeutic radionuclides, could also be delivered instead of blue dye.

In this study, 0.3 ml of $^{99m}$Tc-biotin-liposomes encapsulating blue dye was subcutaneously injected into both foot pads of 6 rabbits. Immediately after injection of the liposomes, 5 mg of avidin was subcutaneously injected into the right foot 2–3 cm proximal to the liposome injection. This study was an asymmetric study because only the right foot was injected with the avidin. Rabbits were imaged for the first hour and at 20 hr after liposome injection. At 20 hr, rabbits were sacrificed and tissue samples were counted in a scintillation well counter.

The popliteal node on the side that received avidin had greatly increased uptake at 20 hours. There was 12.3% in the right node with avidin versus 1.4% in the control left node. This difference was statistically significant at p=0.00003. These results are shown in Table 3. Camera images showed the blue staining of the lymph node on the side of the avidin.

TABLE 3

Tissue Biodistribution Results at 20 Hours
Blue $^{99m}$Tc-Biotin Liposomes Asymmetric Avidin Protocol (n = 6)

|  | % uptake | Standard Error |
| --- | --- | --- |
| Experimental Node | 12.3* | 1.5 |
| Control Node | 1.4 | 0.1 |

*p = 0.00003 vs. control node

The most remarkable finding was the visual appearance of the popliteal node on the side that received the avidin. It was very blue at 20 hours after liposome injection. The blue staining of the lymph node allows it to be readily identified during surgery. The long retention of the blue liposomes in the lymph node has great potential advantages for the variety of protocols which will allow easy recognition of the sentinel lymph node. The liposomes can be injected the day before surgery and will still be visualized the following day during surgery.

Example 16

Repeated Injections are Effective

To assess the effect of repeat injections on the avidin-induced retention of biotin-liposomes in the popliteal lymph nodes, a study was performed with $^{99m}$Tc-biotin-liposomes encapsulating blue dye. These studies were asymmetric and performed in the same manner as Example 13 studies, except that the same group of rabbits (n=4) received repeat injections at baseline, 2 wk and 4 wk. Liposomes were injected into the dorsum of both feet with avidin injected 2 cm proximal on the right foot only. Imaging was performed for the first hour and at 20 hr after liposome injection. Biodistribution was performed by scintigraphic imaging alone since tissue sampling was not possible until the end of the third study in each rabbit.

Results are shown in Table 4. Imaging studies show that there was a statistically significant increase in uptake even after the 3rd injection. There was 4.8% in the side injected with avidin versus 1.0% in the control side Rabbits were imaged at baseline, 2 wk and 4 wk.

TABLE 4

Blue $^{99m}$Tc-Biotin Liposomes Repeat Imaging Studies with Asymmetric Avidin Protocol to Assess Potential Immunological Interference (n = 4)

|  | Initial | SE | 2 Weeks | SE | 4 Weeks | SE |
| --- | --- | --- | --- | --- | --- | --- |
| Experimental Popliteal Node | 6.9* | 1.0 | 5.4Δ | 0.8 | 4.8† | 1.4 |
| Control Popliteal Node | 1.3 | 0.2 | 1.1 | 0.3 | 1.0 | 0.4 |

Uptake based on non-invasive image analysis at 20 hours post injection.
Three studies were repeated at 2 week intervals in the same rabbits.
*p = 0.001 experimental vs. control
Δp = 0.002 experimental vs. control
†p = 0.04 experimental vs. control The repeat studies continued to demonstrate the significantly increased retention of liposomes in the popliteal lymph node on the side of the avidin injection. Since avidin can be highly immunogenic, it was possible that the avidin effect would not function on repeat injections. These studies demonstrate that this avidin technique can be effective even when repeatedly injected in the same animal or person.

Example 17

Specific Targeting of Liposomes

To demonstrate specific targeting of liposomes to a particular node by controlling the location of the avidin injection, 4 rabbits were injected subcutaneously in the dorsum of the foot with 0.3 ml of blue $^{99m}$Tc-biotin-liposomes on one side only. Five minutes later, avidin was subcutaneously injected proximal to the popliteal lymph node in the rabbit thigh. The attempted target was the iliac node.

Results are shown in Table 5. The blue $^{99m}$Tc-biotin-liposomes passed through the popliteal lymph node with retention equal to control studies, but accumulated in the iliac lymph nodes with significantly greater retention than normal. Iliac lymph nodes had greater liposome accumulation than the popliteal lymph node (3.9 versus 1.45 p=0.003). Images demonstrated the increased accumulation in the iliac lymph node compared to the popliteal lymph node

TABLE 5

Tissue Biodistribution Results at 20 Hours - Single Sided Injection in Foot with Avidin Injected in Thigh for Iliac Lymph Node Targeting

| | |
|---|---|
| Iliac Node | 3.9 |
| Popliteal Node | 1.5 | p = 0.003 iliac lymph node vs. popliteal lymph node

This study demonstrates the flexibility of this system for targeting specific lymph nodes regardless of the site of the injection of the liposomes.

Example 18

Targeting Peritoneal Lymph Nodes

To determine if liposomes injected into the peritoneum, followed 30 min later by avidin injected into the peritoneum, would target the lymph nodes that receive lymph that drains from the peritoneum, 2 ml of $^{99m}$Tc-biotin-liposomes encapsulating blue dye were injected into the peritoneum of experimental (n=4) and control rats (n=4). Thirty minutes after liposome injection, 5 mg of avidin in 1 ml of saline was injected into the peritoneum of the experimental group, while the controls received no avidin.

Results are shown in Table 6. The experimental group had a completely different distribution compared to the control group. The control group had an expected distribution of liposomes in the blood, spleen and liver while the experimental group had minimal activity in these organs. The experimental group had significantly elevated lymph node uptake by lymph nodes in the abdomen and the mediastinal regions.

TABLE 6

Tissue Biodistribution Results at 20 Hours after Intraperitoneal Injection of $^{99m}$Tc-Blue Biotin-Liposomes

| | Experimental % Injection dose/organ | (+ Avidin) SE | Control % Injection dose/organ | (− Avidin) SE |
|---|---|---|---|---|
| Spleen | 0.78 | 0.16 | 23.31Λ | 3.92 |
| Blood | 0.17 | 0.03 | 14.08φ | 1.74 |
| Abdominal Nodes | 4.69 | 2.98 | * | |
| Mediastinal Nodes | 2.33 | 0.60 | * | |
| Liver | 7.69 | 1.89 | 9.84 | 0.74 |
| Kidney | 0.78 | 0.16 | 3.94Θ | 0.43 |
| Lung | 0.14 | 0.06 | 0.53⊗ | 0.13 |

* Could not be removed for counting because blue staining of nodes were not present. Only minimal accumulation of blue liposomes in these nodes could have occurred.
Λp = 0.001
φp = 0.0002
Θp = 0.0006
⊗p = 0.04

These methods of targeting liposomes to abdominal and mediastinal lymph nodes may be very important for future drug delivery since most common solid tumors metastasize to these nodes.

Example 19

Targeting Lymph Nodes Draining the Colon

A study was performed to determine if $^{99m}$Tc-blue-biotin liposomes injected into the submucosal tissue of the colon would have increased targeting to the lymph nodes that drain the colon and followed by an avidin injection into submucosal tissue of the colon adjacent to the liposome injection.

Two dogs were studied, one experimental and one control. The dogs were placed under general anesthesia and fiber optic colonoscopy was performed until a portion of the colon near the cecum was visualized on each dog. $^{99m}$Tc-blue-biotin liposomes were injected into the submucosal tissue of the colon causing a blue bleb. Scintigraphic imaging was performed after the initial injection. Five minutes after the initial liposome injection, the experimental animal was injected with 5 mg of avidin into the submucosa of the colon at a location 5 cm distal to the initial liposome injection. Animals were reimaged at 24 hr. Quantitative analysis of the images was performed.

The experimental animal had approximately 8 times more accumulation in the hepatic node compared to the control animal. The biodistribution results are shown in Table 7. A second node was visualized in the abdominal region of the experimental animal that was not visualized in the control animal. Differences between the control and experimental animals were clearly visualized.

TABLE 7

Accumulation of $^{99m}$Tc-Blue-Biotin Liposomes in Lymph Nodes Draining Colon After Colonoscopic Guided Injection of $^{99m}$Tc-Blue-Biotin Liposomes into Colonic Submucosa

| | (n = 1) Experimental (+ Avidin) % localized | (n = 1) Control (− Avidin) % localized |
|---|---|---|
| Initial Injection Site | 23.45 | 25.69 |
| Hepatic Node | 4.41 | 0.58 |
| Iliac Node | 1.22 | not visualized |

Data Determined by Quantitative Image Analysis.

Most carcinomas including colon cancer metastasize first to abdominal lymph nodes. This experiment demonstrates that the lymph nodes draining a region of the colon can be targeted using identification of the cancer with colonoscopic visualization and subsequent injection of the submucosa near the cancer with $^{99m}$Tc-blue-biotin liposomes and avidin. This could greatly increase the delivery of therapeutic agents such as drugs and therapeutic radionuclides to the lymph nodes that drain the region of the colon carcinoma.

While the compositions, compounds, methods, and kits of this invention have been described in terms of preferred embodiments, it will be apparent to those of skill in the art that variations may be applied to the compositions, compounds, methods, and kits, and in the steps of the methods described herein without departing from the concept, spirit, and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

Alving, *J Immuno Methods* 140:1–13, 1991
Baldeschwieler et al., U.S. Pat. No. 4,310,505
Barth et al., *Cancer Res* 50:1061–1070, 1990
Bayer et al., *Methods in Enzymology*, 184: 174–187, 1990
Bookman, *Curr Opin Oncol* 7(5):478–484, 1995
Chinol et al., *Brit J Cancer* 78(2):189–197, 1998
Coleman, *Int J Radiation Onc* 42(4):781–783, 1998
Corley et al., *Biochim Biophys Acta* 1195:149–156, 1994
Cox et al., *Ann Surg* 227(5):645–653, 1998
Daemen, in *Medical Applications of Liposomes*, Lasic and Papahadjopoulos (eds), Elsevier Science B.V., 117–143, 1998
Davis, U.S. Pat. No. 5,792,475
DeCicco et al., *J Nucl Med* 39(12):2080–2084, 1998
DeFrees et al, *J Am Chem Soc*, 118:6101–6104, 1996
DeVita et al., *Cancer: Principles and Practice of Oncology*, 2d ed., J. B. Lippincott Co., Philadelphia, Pa., Chapter 14, 1985
Elmaleh et al., U.S. Pat. No. 5,716,594
Fritzberg et al., U.S. Pat. No. 5,120,526
Gabizon et al., *Bioconjugate Chem*, 10:289–298, 1999
Goldenberg, U.S. Pat. No. 5,698,405
Goldenberg, U.S. Pat. No. 5,736,119
Goldenberg, U.S. Pat. No. 5,776,094
Goodman et al., *The Pharmacological Basis of Therapeutics*, 6th Ed., Gilman et al. (eds), Macmillan Publishing Co., New York, 1980
Goodwin et al., *J Nucl Med* 29(2):226–234, 1988
Goodwin et al., U.S. Pat. No. 4,863,713
Gregoriadis et al, in *Medical Applications of Liposomes*, Lasic and Papahadjopoulos (eds), Elsevier Science B.V., 61–73, 1998
Gregoriadis, Gregory, *The Theory and Practical Application of Adjuvants*, 7: 145–169, 1995
Griffiths et al., *Cancer Res* 51(17):4594–4602, 1991
Griffiths, U.S. Pat. No. 5,482,698
Hader et al., *AORN J* 68:572–588, 1998
Heeremans et al., *Thromb Haemost*, 75(1):134–139, 1996
Hermanson, in *Bioconjugate Techniques*, Academic Press, San Diego, Calif., pg. 552–553, 1996
Hermanson, in *Bioconjugate Techniques*, Academic Press, San Diego, Calif., pg. 548–549, 1996
Hirnle, *Hybridoma*, 16(1): 127–132, 1997
Hnatowich et al, *J Nucl Med* 28(8):1294–1302, 1987
Hnatowich et al., *Nucl Med Biol* 20:189–195, 1993
Hope et al., *Biochim et Biophys Acta*, 812:55–65, 1985
Illum, U.S. Pat. No. 4,904,479
Jeong et al., in *Handbook of Targeted Delivery of Imaging Agents*, Chap. 18, 305–319, CRC Press, 1995
Johnsson, et al., *J Liposome Res* 9(1), 53–79, 1999
Kalofonos et al., *J Nucl Med* 31(11):1791–1796, 1990
Kang et al., *J Pharm Exptl Therapeutics* 269:344–350, 1994
Klibanov et al., *J Nucl Med* 29(12):1951–1956, 1988
Klibanov, *Adv Drug Delivery Rev* 37:139–157, 1999
Kohno et al., *J Infect Chemother*, 4:159–173, 1998
Komura et al., *Melanoma Res* 1(5–6):397–403, 1992
Kotz, *J Nucl Med* 39(12):13N–21N, 1998
Krag et al., *N Engl J Med* 339(14):941–946, 1998
Krag et al., *Surg Oncol* 2:335–339, 1993
Krause, *Adv Drug Delivery Rev* 37:159–173, 1999
Kung et al., *Biochim Biophys Acta* 839:105–109, 1985
Lanza, U.S. Pat. No. 5,690,907
Lasic et al., in *Vesicles*, Rosoff(ed), Marcel Dekker, New York, 477–489, 1996
Leserman et al, in *Liposomes From Biophysics to Therapeutics*, Ostro (ed), Marcel Dekker, New York, pg. 157–194, 1987
Lindblad, *Theory Prac Appl Adjuvants* 2:21–35, 1995
Litzinger et al., *Biochim Biophys Acta* 1127(3):249–254, 1992
Magnani et al, *J Nucl Med* 37(6): 967–971, 1996
Mayer et al, *Biochim Biophys Acta* 858:161–168, 1986
Mayhew et al., *Methods Enzym* 149:64–77, 1987
Meares et al., *Br J Cancer Suppl* 10:21–26, 1990
Moghimi et al., *FESB Letters* 344:25–30, 1994
Moghimi et al., *Prog Biophys Molec Biol* 65:221–249, 1996
Morton et al., *Arch Surg* 127(4):392–399, 1992
Morton et al., *Surg Oncol Clin N Am* 1:247–59, 1992
New, *Preparation of Liposomes in Liposomes: A Practical Approach*, New (ed), Oxford University Press, NY, 33–104, 1990
Oehr et al., *J Nucl Med* 29:728, 1988
Ogihara-Umeda et al., *Cancer Detection and Prevention* 21(6):490–496, 1997
Oussoren et al., *Biochim Biophys Acta* 1328–261–272, 1997
Oussoren et al., *Pharm Res*, 14(10):1479–1484, 1997
Paganelli et al., *Cancer Res* 51(21):5960–5966, 1991
Paganelli et al., *Eur J Nucl Med* 24(3):350–351, 1997
Paganelli et al., *Eur J Nucl Med*, 19(5):322–329, 1992
Paganelli et al., in *Handbook of Targeted Delivery of Imaging Agents*, Chap. 17, CRC Press, 289–303, 1995
Paganelli et al., *Nucl Med Commun* 12(3):211–234, 1991
Papisov et al., *Crit Rev Ther Drug Carrier Syst* 13(1&2): 57–84, 1996
Phillips et al., in *Handbook of Targeted Delivery of Imaging Agents*, Chap. 10, CRC Press, 149–173, 1995
Pykett, *Sci Am* 246(5):78–88, 1982
Rao et al., *Science* 280(5364):708–711, 1999
Rawls, *C&EN*, 26–29, Mar. 22, 1999
Reintgen, *J Nucl Med* 39(12):22N–36N, 1998
*Remington's Pharmaceutical Sciences*, 15th Ed., pp. 1035–1038 and 1570–1580
Runge et al., *Am J Roentgeno* 141(6):1209–1215, 1983
Schechter et al., *Int J Cancer* 48(2): 167–172, 1991
Schuber, in *Liposomes as Tools in Basic Research and Industry*, Philippot and Schuber (eds), CRC Press, Boca Raton, 21–39, 1995
Sinitsyn et al, *J Nucl Med* 30(1):66–69, 1989
Sinkula et al., *J Pharm Sci* 64:181–210, 1975
Stickney et al., *Cancer Res* 51(24):6650–6655, 1991
Strand, *Crit Rev Ther Drug Carrier Syst* 6(3):211–237, 1989
Tanabe et al., *Adv Surg* 31:79–103, 1998
Terskikh et al., *Proc Natl Acad Sci USA* 94:1663–1668, 1997
Tiong et al., *Vaccine* 11(4):425–430, 1993
Tiourina et al., *Eur J Nucl Med* 25:1224–1231, 1998
Van der Veen et al., *Br J Surg* 81(12):1769–1770, 1994
Veronesi et al., *Lancet* 349(9069):1864–1867, 1997
Weiss et al., *Lymphatic System Metastases*, Hall, Boston, 1988
Wolf, in *Handbook of Targeted Delivery of Imaging Agents*, Chap. 21, 366–384, CRC Press, 1995
Woodle et al., in *Medical Applications of Liposomes*, Lasic and Papahadjopoulos (eds), Elsevier Science B.V., 429–449, 1998
Yoffrey et al., *Lymphatics, lymph and the Lymphomyeloid complex*, Academic Press, London, 1970
Yuan et al., *Cancer Res* 51(12):3119–3130, 1991

The invention claimed is:

1. A method for delivery and retention of an active agent in one or more targeted lymph nodes, comprising:
   a) injecting into a mammal a first composition comprising a biotin conjugated to a liposome comprising a diameter of less than 500 nm; and
   b) injecting into said mammal a second composition comprising an avidin, wherein said avidin binds to said biotin, and
   wherein the active agent is bound to or encapsulated in either said liposome or said avidin, and wherein the avidin aggregates with the liposome-biotin complex at, or just prior to reaching, the one or more targeted lymph nodes.

2. The method of claim 1, wherein the liposome comprises phospholipid.

3. The method of claim 2, wherein the phospholipid comprises DPPC or DSPC.

4. The method of claim 1, wherein the liposome comprises cholesterol.

5. The method of claim 1, wherein the liposome encapsulates or is bound to the active agent.

6. The method of claim 1, wherein the active agent is chosen from the group consisting of diagnostic agents, therapeutic agents, photoactivated dyes, cytotoxic agents, biological response modifiers, hormone suppressants, prodrugs, dyes for visual detection, radiosensitizers, radioprotectors, DNA, RNA, antigens, radioisotopes and neutron capture isotopes.

7. The method of claim 6, wherein the active agent is chosen from the group consisting of radioisotopes and dyes.

8. The method of claim 6, wherein the active agent is chosen from the group consisting of diagnostic agents and dyes for visual detection.

9. The method of claim 6, wherein the active agent is chosen from the group consisting of photoactivated dyes, cytotoxic agents, biological response modifiers, hormone suppressants, prodrugs, radiosensitizers, radioprotectors, DNA, RNA, and neutron capture agents.

10. The method of claim 6, wherein the active agent comprises a radioisotope and a dye.

11. The method of claim 1, wherein the avidin is bound to said active agent.

12. The method of claim 1, wherein the liposome comprises a size range of 50 to 300 nm.

13. The method of claim 1, wherein the first and second compositions are administered by subcutaneous, subdermal, submucosal, intraperitoneal, intrapleural, intraarticular, intramucosal, intramuscular, intradermal, intratumoral, interstitial, intraorgan, intracavitary, intralymphatic, intralesion, or intraosseal injection.

14. A method for detecting one or more sentinel lymph nodes comprising:
   a) injecting into a mammal a first composition comprising a biotin conjugated to a liposome comprising a diameter of less than 500 nm; and
   b) injecting into said mammal a second composition comprising avidin, wherein said avidin binds to said biotin,
   wherein a radioisotope or a dye is bound to or encapsulated in either said liposome or said avidin, and wherein the avidin aggregates with the liposome-biotin complex at, or just prior to reaching, the one or more sentinel lymph nodes.

15. The method of claim 14, wherein the liposome encapsulates the radioisotope or dye.

16. The method of claim 15, wherein the liposome encapsulates the radioisotope.

17. The method of claim 15, wherein the detection agent comprises a radioisotope and a dye.

18. The method of claim 14, wherein the avidin is bound to said radioisotope or dye.

19. The method of claim 18, wherein the avidin is bound to said radioisotope.

20. The method of claim 14, wherein the liposome comprises a size range of 50 to 300 nm.

21. The method of claim 14, wherein the first and second compositions are administered by subcutaneous, subdermal, submucosal, intraperitoneal, intrapleural, intraarticular, intramucosal, intramuscular, intradermal, intratumoral, interstitial, intraorgan, intracavitary, intralymphatic, intralesion, or intraosseal injection.

* * * * *